US007838023B2

(12) United States Patent
Garvey et al.

(10) Patent No.: US 7,838,023 B2
(45) Date of Patent: Nov. 23, 2010

(54) FUROXAN COMPOUNDS, COMPOSITIONS AND METHODS OF USE

(75) Inventors: David S. Garvey, Dover, MA (US); Ramani R. Ranatunge, Lexington, MA (US)

(73) Assignee: NitroMed, Inc., Charlotte, NC (US)

( * ) Notice: Subject to any disclaimer, the term of this patent is extended or adjusted under 35 U.S.C. 154(b) by 101 days.

(21) Appl. No.: 12/093,561

(22) PCT Filed: Nov. 16, 2006

(86) PCT No.: PCT/US2006/044680

§ 371 (c)(1), (2), (4) Date: May 13, 2008

(87) PCT Pub. No.: WO2007/059311

PCT Pub. Date: May 24, 2007

(65) Prior Publication Data

US 2008/0268014 A1    Oct. 30, 2008

Related U.S. Application Data

(60) Provisional application No. 60/736,871, filed on Nov. 16, 2005.

(51) Int. Cl.
| A61K 9/00 | (2006.01) |
| A61K 31/4245 | (2006.01) |
| A61K 31/502 | (2006.01) |
| A61K 33/00 | (2006.01) |
| A61P 9/00 | (2006.01) |
| C07D 271/08 | (2006.01) |

(52) U.S. Cl. .................. 424/423; 514/248; 514/364; 548/125; 424/718

(58) Field of Classification Search ............. 424/423, 424/718; 514/248, 364; 548/125
See application file for complete search history.

(56) References Cited

U.S. PATENT DOCUMENTS

| 4,416,893 | A | 11/1983 | Schonafinger et al. |
| 4,780,401 | A | 10/1988 | Heusser et al. |
| 4,845,079 | A | 7/1989 | Luly et al. |
| 4,885,292 | A | 12/1989 | Ryono et al. |
| 4,894,437 | A | 1/1990 | TenBrink |
| 4,980,283 | A | 12/1990 | Huang et al. |
| 5,034,512 | A | 7/1991 | Hudspeth et al. |
| 5,036,053 | A | 7/1991 | Himmelsbach et al. |
| 5,036,054 | A | 7/1991 | Kaltenbronn et al. |
| 5,055,466 | A | 10/1991 | Weller, III et al. |
| 5,063,207 | A | 11/1991 | Doherty et al. |
| 5,063,208 | A | 11/1991 | Rosenberg et al. |
| 5,064,965 | A | 11/1991 | Ocain et al. |
| 5,066,643 | A | 11/1991 | Abeles et al. |
| 5,071,837 | A | 12/1991 | Doherty et al. |
| 5,075,451 | A | 12/1991 | Ocain et al. |
| 5,089,471 | A | 2/1992 | Hanson et al. |
| 5,095,006 | A | 3/1992 | Bender et al. |
| 5,095,119 | A | 3/1992 | Ocain et al. |
| 5,098,924 | A | 3/1992 | Poss |
| 5,104,869 | A | 4/1992 | Albright et al. |
| 5,106,835 | A | 4/1992 | Albright et al. |
| 5,114,937 | A | 5/1992 | Hamby et al. |
| 5,116,835 | A | 5/1992 | Ruger et al. |
| 5,262,165 | A | 11/1993 | Govil et al. |
| 5,284,872 | A | 2/1994 | Sandrock et al. |
| 5,344,991 | A | 9/1994 | Reitz et al. |
| 5,380,738 | A | 1/1995 | Norman et al. |
| 5,380,758 | A | 1/1995 | Stamler et al. |
| 5,389,655 | A | 2/1995 | Schonafinger et al. |
| 5,393,790 | A | 2/1995 | Reitz et al. |
| 5,409,944 | A | 4/1995 | Black et al. |
| 5,428,061 | A | 6/1995 | Sandrock et al. |
| 5,434,178 | A | 7/1995 | Talley et al. |
| 5,436,265 | A | 7/1995 | Black et al. |
| 5,466,823 | A | 11/1995 | Talley et al. |
| 5,474,995 | A | 12/1995 | Ducharme et al. |

(Continued)

FOREIGN PATENT DOCUMENTS

EP    0574726    12/1993

(Continued)

OTHER PUBLICATIONS

Cerecetto et al., Archiv der Pharmazie (Weinheim, Germany), (2000), vol. 333(11), p. 387-393.*

(Continued)

Primary Examiner—Yong Chu
(74) Attorney, Agent, or Firm—Wilmer Cutler Pickering Hale and Dorr LLP

(57) ABSTRACT

The invention provides novel furoxan compounds, or pharmaceutically acceptable salts thereof, and novel compositions comprising at least one compound, and, optionally, at least one nitric oxide enhancing compound and/or at least one therapeutic agent. The compounds and compositions of the invention can also be bound to a matrix. The invention also provides methods for (a) treating cardiovascular diseases; (b) inhibiting platelet aggregation and platelet adhesion caused by the exposure of blood to a medical device; (c) treating pathological conditions resulting from abnormal cell proliferation; (d) treating transplantation rejections, (e) treating autoimmune, inflammatory, proliferative, hyperproliferative or vascular diseases; (f) reducing scar tissue or for inhibiting wound contraction; (g) treating diseases resulting from oxidative stress; (h) treating endothelial dysfunctions; and (j) treating diseases caused by endothelial dysfunctions.

9 Claims, No Drawings

U.S. PATENT DOCUMENTS

| | | | |
|---|---|---|---|
| 5,510,368 | A | 4/1996 | Lau et al. |
| 5,536,752 | A | 7/1996 | Ducharme et al. |
| 5,550,142 | A | 8/1996 | Ducharme et al. |
| 5,552,422 | A | 9/1996 | Gauthier et al. |
| 5,604,253 | A | 2/1997 | Lau et al. |
| 5,604,260 | A | 2/1997 | Guay et al. |
| 5,639,780 | A | 6/1997 | Lau et al. |
| 5,650,447 | A | 7/1997 | Keefer et al. |
| 5,661,129 | A | 8/1997 | Feelisch et al. |
| 5,665,077 | A | 9/1997 | Rosen et al. |
| 5,703,073 | A | 12/1997 | Garvey et al. |
| 5,705,583 | A | 1/1998 | Bowers et al. |
| 5,770,645 | A | 6/1998 | Stamler et al. |
| 5,797,887 | A | 8/1998 | Rosen et al. |
| 5,807,847 | A | 9/1998 | Thatcher et al. |
| 5,824,049 | A | 10/1998 | Ragheb et al. |
| 5,837,008 | A | 11/1998 | Berg et al. |
| 5,874,437 | A | 2/1999 | Garvey et al. |
| 5,883,122 | A | 3/1999 | Thatcher et al. |
| 5,886,026 | A | 3/1999 | Hunter et al. |
| 5,910,316 | A | 6/1999 | Keefer et al. |
| 5,932,538 | A | 8/1999 | Garvey et al. |
| 5,932,598 | A | 8/1999 | Talley et al. |
| 5,948,433 | A | 9/1999 | Burton et al. |
| 5,958,926 | A | 9/1999 | Garvey et al. |
| 5,994,294 | A | 11/1999 | Garvey et al. |
| 5,994,444 | A | 11/1999 | Trescony et al. |
| 6,010,715 | A | 1/2000 | Wick et al. |
| 6,057,347 | A | 5/2000 | Garvey et al. |
| 6,071,531 | A | 6/2000 | Jona et al. |
| 6,087,479 | A | 7/2000 | Stamler et al. |
| 6,133,272 | A | 10/2000 | Garvey et al. |
| 6,153,252 | A | 11/2000 | Hossainy et al. |
| 6,172,060 | B1 | 1/2001 | Garvey et al. |
| 6,172,068 | B1 | 1/2001 | Garvey et al. |
| 6,177,428 | B1 | 1/2001 | Garvey et al. |
| 6,197,778 | B1 | 3/2001 | Garvey et al. |
| 6,197,782 | B1 | 3/2001 | Garvey et al. |
| 6,211,179 | B1 | 4/2001 | Garvey et al. |
| 6,221,881 | B1 | 4/2001 | Garvey et al. |
| 6,232,321 | B1 | 5/2001 | Garvey et al. |
| 6,232,336 | B1 | 5/2001 | Hrabie et al. |
| RE37,234 | E | 6/2001 | Garvey et al. |
| 6,297,260 | B1 | 10/2001 | Bandarage et al. |
| 6,316,457 | B1 | 11/2001 | Garvey et al. |
| 6,331,542 | B1 | 12/2001 | Carr et al. |
| 6,633,272 | B1 | 10/2003 | Kumagawa et al. |

FOREIGN PATENT DOCUMENTS

| | | |
|---|---|---|
| EP | 0581062 | 2/1994 |
| EP | 0683159 | 11/1995 |
| WO | WO 92/05179 | 4/1992 |
| WO | WO-94/03387 | 2/1994 |
| WO | WO-94/15723 | 7/1994 |
| WO | WO-94/20480 | 9/1994 |
| WO | WO-94/26731 | 11/1994 |
| WO | WO-94/27980 | 12/1994 |
| WO | WO-95/00501 | 1/1995 |
| WO | WO-95/15316 | 6/1995 |
| WO | WO-96/03387 | 2/1996 |
| WO | WO-96/03388 | 2/1996 |
| WO | WO-96/06840 | 3/1996 |
| WO | WO-96/21667 | 7/1996 |
| WO | WO-96/31509 | 10/1996 |
| WO | WO-96/36623 | 11/1996 |
| WO | WO-97/14691 | 4/1997 |
| WO | WO-97/16435 | 5/1997 |
| WO | WO-97/27749 | 8/1997 |
| WO | WO-97/46521 | 12/1997 |
| WO | WO-98/09972 | 3/1998 |
| WO | WO-98/19672 | 5/1998 |
| WO | WO-98/24427 | 6/1998 |
| WO | WO-99/62510 | 12/1999 |
| WO | WO-00/28988 | 5/2000 |
| WO | WO-00/50037 | 8/2000 |
| WO | WO-00/54756 | 9/2000 |
| WO | WO-01/45703 | 6/2001 |
| WO | WO-01/87343 | 11/2001 |
| WO | WO-03/013432 A | 2/2003 |
| WO | WO-03/017996 | 3/2003 |
| WO | WO-2005/018561 | 3/2005 |
| WO | WO-2005060603 | 7/2005 |

OTHER PUBLICATIONS

PCT International Search Report for Application No. PCT/US06/44680 dated Nov. 6, 2007.
Arzneim. Forsch. Drug Res., 47(II):849-854 (1997).
Biochemical Pharmacol., 43:1281-1288 (1992).
Bioorg & Med. Chem., 8:1727-1732 (2000).
Bioorg & Med. Chem. Letts., 13:4179-4186 (2003).
Br. J. Pharmacol., 114:816-820 (1995).
Brideau, et al., Inflamm Res., 45:68-74 (1996).
Drug Facts and Comparisons, Inc., St. Louis, MO (1993 Ed.).
Farrer, W.V., J. Chem. Soc., 904-906 (1964).
Goodman and Gilman, The Pharmacological Basis of Therapeutics (9th Edition), McGraw-Hill, pp. 617-657 (1995).
Greene and Wuts, Protective Groups in Organic Synthesis, Third Edition, John Wiley & Sons, New York (1999).
Helv. Chim. Acta., 79:1803-1817 (1996).
Ignarro, et al., Proc. Natl. Acad. Sci. USA, 84:9265-9269 (1987).
Il Farmaco, 52:339-341 (1997).
Il Farmaco, 52:405-510 (1997).
J. Heterocyclic Chem., 10:587-590 (1973).
J. Heterocyclic Chem., 14:1415-1416 (1977).
J. Heterocyclic Chem., 33:327-334 (1996).
J. Med. Chem., 35:3296-3300 (1992).
J. Med. Chem., 37:4412-4416 (1994).
J. Med. Chem., 38:4944-4949 (1995).
J. Med. Chem., 40:463-469 (1997).
J. Med. Chem., 41:5393-5401 (1998).
J. Med. Chem., 42:1422-1427 (1999).
J. Med. Chem., 42:1941-1950 (1999).
J. Med. Chem., 44:3463-3468 (2001).
J. Med. Chem., 46:747-754 (2003).
J. Med. Chem., 46:3762-3765 (2003).
J. Med. Chem., 47:1840-1846 (2004).
J. Med. Chem., 47:2688-2693 (2004).
Merck Index on CD-ROM, 13th Edition, (2001).
Oae, et al., Org. Prep. Proc. Int., 15(3):165-198 (1983).
Palmer, et al., Nature, 327:524-526 (1987).
Pharmaceutical Research, 14:1750-1758 (1997).
Pharmaceutical Res., 18:157-165 (2001).
Smith and Mar., March's Advanced Organic Chemistry, Reactions, Mechanisms and Structure, Fifth Edition, John Wiley & Sons, Yew York (2001).
Synthetic Comm., 1:121-124 (1971).
Tet. Letts., 36:3337-3340 (1995).
The Physician's Desk Reference (49th Ed.), Medical Economics Company, Inc., Oradel, NJ (1995).
European Application No. 06837911 Supplementary Search Report, dated Sep. 2, 2009 (2 pages).

* cited by examiner

FUROXAN COMPOUNDS, COMPOSITIONS AND METHODS OF USE

RELATED APPLICATIONS

This application is a 371 National Stage of PCT/US2006/44680 filed Nov. 16, 2006, which claims priority under 35 USC §119 to U.S. Application No. 60/736,871 filed Nov. 16, 2005; the disclosure of which is incorporated by reference herein in its entirety.

FIELD OF THE INVENTION

The invention describes novel furoxan compounds comprising at least two furoxan moieties, or pharmaceutically acceptable salts thereof, and novel compositions comprising at least one compound, and, optionally, at least one nitric oxide enhancing compound and/or at least one therapeutic agent. The invention also provides novel compositions and kits comprising at least one furoxan compound of the invention, and, optionally, at least one nitric oxide enhancing compound and/or at least one therapeutic agent. The compounds and compositions of the invention can also be bound to a matrix. The invention also provides methods for (a) treating cardiovascular diseases; (b) inhibiting platelet aggregation and platelet adhesion caused by the exposure of blood to a medical device; (c) treating pathological conditions resulting from abnormal cell proliferation; (d) treating transplantation rejections, (e) treating autoimmune, inflammatory, proliferative, hyperproliferative or vascular diseases; (f) reducing scar tissue or for inhibiting wound contraction; (g) treating diseases resulting from oxidative stress; (h) treating endothelial dysfunctions; and (j) treating diseases caused by endothelial dysfunctions.

BACKGROUND OF THE INVENTION

Despite considerable efforts to develop nonthrombogenic materials, no synthetic material has been created that is free from this effect. In addition, the use of anticoagulant and platelet inhibition agents has been less than satisfactory in preventing adverse consequences resulting from the interaction between blood and artificial surfaces. Consequently, a significant need exists for the development of additional methods for inhibiting platelet deposition and thrombus formation on artificial surfaces.

There is a need in the art for effective methods for treating cardiovascular diseases and disorders, particularly, restenosis and atherosclerosis. The invention is directed to these, as well as other, important ends.

SUMMARY OF THE INVENTION

The invention provides novel furoxan compounds comprising at least two furoxan moieties, and pharmaceutically acceptable salts thereof. The invention also provides compositions comprising the novel compounds described herein in a pharmaceutically acceptable carrier.

The invention is also based on the discovery that administering at least one furoxan compound comprising at least two furoxan moieties, or a pharmaceutically acceptable salt thereof, and, optionally, at least one nitric oxide enhancing compound improves the properties of the furoxan compound. Nitric oxide enhancing compounds include, for example, S-nitrosothiols, nitrites, nitrates, N-oxo-N-nitrosamines, furoxans, sydnonimines, SPM 3672, SPM 4757, SPM 5185, SPM 5186 and analogues thereof, substrates of the various isozymes of nitric oxide synthase, and nitroxides. Thus, another embodiment of the invention provides compositions comprising at least one furoxan compound of the invention and at least one nitric oxide enhancing compound. The invention also provides for such compositions in a pharmaceutically acceptable carrier.

The invention provides compositions comprising at least one furoxan compound of the invention, and, optionally, at least one nitric oxide enhancing compound and/or at least one therapeutic agent, including, but not limited to, thrombolytic agents, antimicrobial compounds, antiproliferative agents, antisecretory agents, anti-cancer chemotherapeutic agents, steroids, immunosuppressive agents, radiotherapeutic agents, heavy metals functioning as a radiopaque agent, biologic agents, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In one embodiment the at least one therapeutic agent is selected from the group consisting of a thrombolytic agent, an antimicrobial compound, an antiproliferative agent, an anti-cancer chemotherapeutic agent, a steroid, an immunosuppressive agents, an antioxidant, an antithrombotic and vasodilator compound, a hydralazine compound, and a platelet reducing agent. The invention also provides for such compositions in a pharmaceutically acceptable carrier.

Another embodiment of the invention provides compositions comprising an effective amount of at least one furoxan compound of the invention, and at least one therapeutic agent selected from the group consisting of a thrombolytic agent, an antimicrobial compound, an antiproliferative agent, an anti-cancer chemotherapeutic agent, a steroid, an immunosuppressive agents, an antioxidant, an antithrombotic and vasodilator compound, a hydralazine compound, and a platelet reducing agent. The invention also provides for such compositions in a pharmaceutically acceptable carrier.

Another embodiment of the invention describes compositions and methods for making compositions comprising at least one furoxan compound of the invention and, optionally, at least one nitric oxide enhancing compound and/or at least one therapeutic agent that are bound to a natural or synthetic matrix, which can be applied with specificity to a biological site of interest. For example, the matrix containing the compounds or compositions of the invention (e.g. the furoxan compounds) can be used to coat the surface of a medical device that comes into contact with blood (including blood components, blood products and the like), vascular or non-vascular tissue.

The invention provides methods for (a) treating cardiovascular diseases; (b) inhibiting platelet aggregation and platelet adhesion caused by the exposure of blood to a medical device; (c) treating pathological condition resulting from abnormal cell proliferation; (d) treating transplantation rejections, (e) treating inflammatory disease; (f) reducing scar tissue or for inhibiting wound contraction; (g) treating diseases resulting from oxidative stress; (h) treating endothelial dysfunctions; and (j) treating diseases caused by endothelial dysfunctions in a patient in need thereof comprising administering to the patient an effective amount of at least one furoxan compound comprising at least two furoxan moieties, and, optionally, at least one therapeutic agent, such as, for example, thrombolytic agents, antimicrobial compounds, antiproliferative agents, antisecretory agents, anti-cancer chemotherapeutic agents, steroids, immunosuppressive agents, radiotherapeutic agents, heavy metals functioning as a radiopaque agent, biologic agents, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. The methods can optionally further comprises the administration of at least one nitric oxide enhancing compound. In this embodiment of the invention, the methods can involve (i) administering the furoxan compounds, (ii) administering the furoxan compounds and nitric oxide enhancing compounds, (iii) administering the furoxan compounds and therapeutic agents, or (iv) administering the furoxan compounds, nitric oxide enhancing compounds, and therapeutic agents. In one embodiment the at least one therapeutic agent is selected from the group consisting of a thrombolytic agent, an antimicrobial compound, an antiproliferative agent, an anti-cancer chemotherapeutic agent, a steroid, an immunosuppressive agents, an antioxidant, an antithrombotic and vasodilator compound, a hydralazine compound, and a platelet reducing agent. The furoxan compounds, nitric oxide enhancing compounds, and/or therapeutic agents can be administered separately or as components of the same composition in one or more pharmaceutically acceptable carriers.

Another embodiment of the invention provides kits comprising at least one furoxan compound comprising at least two furoxan moieties, and, optionally, at least one nitric oxide enhancing compound. The kit can further comprise at least one therapeutic agent; such as, for example, thrombolytic agents, antimicrobial compounds, antiproliferative agents, antisecretory agents, anti-cancer chemotherapeutic agents, steroids, immunosuppressive agents, radiotherapeutic agents, heavy metals functioning as a radiopaque agent, biologic agents, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. The furoxan compound, the nitric oxide enhancing compound and/or therapeutic agent, can be separate components in the kit or can be in the form of a composition in one or more pharmaceutically acceptable carriers.

These and other aspects of the invention are described in detail herein.

DETAILED DESCRIPTION OF THE INVENTION

As used throughout the disclosure, the following terms, unless otherwise indicated, shall be understood to have the following meanings.

"Cardiovascular disease or disorder" refers to any cardiovascular disease or disorder known in the art, including, but not limited to, heart failure, restenosis, hypertension (e.g. pulmonary hypertension, labile hypertension, idiopathic hypertension, low-renin hypertension, salt-sensitive hypertension, low-renin, salt-sensitive hypertension, thromboembolic pulmonary hypertension; pregnancy-induced hypertension; renovascular hypertension; hypertension-dependent end-stage renal disease, hypertension associated with cardiovascular surgical procedures, hypertension with left ventricular hypertrophy, and the like), diastolic dysfunction, coronary artery disease, myocardial infarctions, cerebral infarctions, atherosclerosis, atherogenesis, cerebrovascular disease, angina, (including chronic, stable, unstable and variant (Prinzmetal) angina pectoris), aneurysm, ischemic heart disease, cerebral ischemia, myocardial ischemia, thrombosis, platelet aggregation, platelet adhesion, smooth muscle cell proliferation, vascular or non-vascular complications associated with the use of medical devices, wounds associated with the use of medical devices, vascular or non-vascular wall damage, peripheral vascular disease, neointimal hyperplasia following percutaneous transluminal coronary angiograph, vascular grafting, coronary artery bypass surgery, thromboembolic events, post-angioplasty restenosis, coronary plaque inflammation, hypercholesterolemia, embolism, stroke, shock, arrhythmia, atrial fibrillation or atrial flutter, thrombotic occlusion and reclusion cerebrovascular incidents, left ventricular dysfunction and hypertrophy, and the like.

"Restenosis" is a cardiovascular disease or disorder that refers to the closure of a peripheral or coronary artery following trauma to the artery caused by an injury such as, for example, angioplasty, balloon dilation, atherectomy, laser ablation treatment or stent insertion. For these angioplasty procedures, restenosis occurs at a rate of about 30-60% depending upon the vessel location, lesion length and a number of other variables. Restenosis can also occur following a number of invasive surgical techniques, such as, for example, transplant surgery, vein grafting, coronary artery bypass surgery, endarterectomy, heart transplantation, balloon angioplasty, atherectomy, laser ablation, endovascular stenting, and the like.

"Atherosclerosis" is a form of chronic vascular injury in which some of the normal vascular smooth muscle cells in the artery wall, which ordinarily control vascular tone regulating blood flow, change their nature and develop "cancer-like" behavior. These vascular smooth muscle cells become abnormally proliferative, secreting substances, such as growth factors, tissue-degradation enzymes and other proteins, which enable them to invade and spread into the inner vessel lining, blocking blood flow and making that vessel abnormally susceptible to being completely blocked by local blood clotting, resulting in the death of the tissue served by that artery.

"Autoimmune, inflammatory, proliferative, hyperproliferative or vascular diseases" refers to any autoimmune, inflammatory, proliferative or hyperproliferative disease or disorder known in the art whether of a chronic or acute nature, including, but not limited to, rheumatoid arthritis, restenosis, lupus erythematosus, systemic lupus erythematosus, Hashimotos thyroiditis, myasthenia gravis, diabetes mellitus, uveitis, nephritic syndrome, multiple sclerosis; inflammatory skin diseases, such as, for example, psoriasis, dermatitis, contact dermatitis, eczema and seborrhea; surgical adhesion; tuberculosis; inflammatory lung diseases, such as asthma, pneumoconiosis, chronic obstructive pulmonary disease, emphysema, bronchitis, nasal polyps and pulmonary fibrosis; inflammatory bowel disease, such as Crohn's disease and ulcerative colitis; graft rejections; inflammatory diseases that affect or cause obstruction of a body passageway, such as vasculitis, Wegener's granulomatosis and Kawasaki disease; inflammation of the eye, nose or throat, such as neovascular diseases of the eye including neovascular glaucoma, proliferative diabetic retinopathy, retrolental fibroblasia, macular degeneration, reduction of intraocular pressure, corneal neovascularization, such as corneal infections; immunological processes, such as graft rejection and Steven-Johnson's syndrome, alkali burns, trauma and inflammation (of any cause); fungal infections, such as, for example, infections caused by *Candida, Trichophyton, Microsporum, Eepidermophyton, Cryptococcus, Aspergillus, Coccidiodes, Paracocciciodes, Histoplasma or Blastomyces* spp; food related allergies, such as, for example, migraine, rhinitis and eczema; vascular diseases, such as arotic aneurysm. A description of inflammatory diseases can also be found in WO 92/05179, WO 98/09972, WO 98/24427, WO 99/62510 and U.S. Pat. No. 5,886,026, the disclosures of each of which are incorporated herein in their entirety.

"Pathological conditions resulting from abnormal cell proliferation" refers to any abnormal cellular proliferation of malignant or non-malignant cells in various tissues and/or organs, including but not limited to, muscle, bone, conjunctive tissues, skin, brain, lungs, sexual organs, lymphatic system, renal system, mammary cells, blood cells, liver, the digestive system, pancreas, thyroid, adrenal glands and the like. These pathological conditions can also include psoriasis; solid tumors; ovarian, breast, brain, prostate, colon, esophageal, lung, stomach, kidney and/or testicular cancer; Karposi's sarcoma, cholangiocarcinoma; choriocarcinoma; neoblastoma; Wilm's tumor; Hodgkin's disease; melanomas; multiple myelomas; chronic lymphocytic leukemias, and acute or chronic granulocytic lymphomas. The treatment of "pathological conditions resulting from abnormal cell proliferation" includes, but is not limited to, reduction of tumor size, inhibition of tumor growth and/or prolongation of the survival time of tumor-bearing patients.

"Transplantation" refers to the transplant of any organ or body part, including but not limited to, heart, kidney, liver, lung, bone marrow, cornea and skin transplants.

"Artificial surface" refers to any natural or synthetic material contained in a device or apparatus that is in contact with blood, vasculature or other tissues.

"Blood" includes blood products, blood components and the like.

"Medical device" refers to any intravascular or extravascular medical devices, medical instruments, medical product, foreign bodies including implants and the like, having a surface that comes in contact with tissue, blood or bodily fluids in the course of its use or operation. Examples of intravascular medical devices and instruments include balloons or catheter tips adapted for insertion, prosthetic heart valves, sutures, surgical staples, synthetic vessel grafts, stents (e.g. Palmaz-Schatz, Wiktor, Crown, Mutlilink, GFX stents), stent grafts, vascular or non-vascular grafts, shunts, aneurysm fillers (including GDC, Guglilmi detachable coils), intraluminal paving systems, guide wires, embolic agents (for example, polymeric particles, spheres and liquid embolics), filters (for example, vena cava filters), arteriovenous shunts, artificial heart valves, artificial implants including, but not limited to, prostheses, foreign bodies introduced surgically into the blood vessels, at vascular or non-vascular sites, leads, pacemakers, implantable pulse generators, implantable cardiac defibrillators, cardioverter defibrillators, defibrillators, spinal stimulators, brain stimulators, sacral nerve stimulators, chemical sensors, breast implants, interventional cardiology devices, catheters, amniocentesis and biopsy needles, and the like. Examples of extravascular medical devices and instruments include plastic tubing, dialysis bags or membranes whose surfaces come in contact with the blood stream of a patient, blood oxygenators, blood pumps, blood storage bags, blood collection tubes, blood filters and/or filtration devices, drug pumps, contact lenses, and the like. The term "medical device" also includes bandages or any external device that can be applied directed to the skin.

"Platelet adhesion" refers to the contact of a platelet with a foreign surface, including any artificial surface, such as a medical device, as well as injured vascular or non-vascular surfaces, such as collagen. Platelet adhesion does not require platelet activation. Unactivated, circulating platelets will adhere to injured vascular or non-vascular surfaces or artificial surfaces via binding interactions between circulating von Willdebrand factor and platelet surface glycoprotein Ib/IX.

"Platelet aggregation" refers to the binding of one or more platelets to each other. Platelet aggregation is commonly referred to in the context of generalized atherosclerosis, not with respect to platelet adhesion on vasculature damaged as a result of physical injury during a medical procedure. Platelet aggregation requires platelet activation which depends on the interaction between the ligand and its specific platelet surface receptor.

"Platelet activation" refers either to the change in conformation (shape) of a cell, expression of cell surface proteins (e.g., the IIb/IIIa receptor complex, loss of GPIb surface protein), and secretion of platelet derived factors (e.g., serotonin, growth factors).

"Diseases resulting from oxidative stress" refers to any disease that involves the generation of free radicals or radical compounds, such as, for example, atherogenesis, atheromatosis, arteriosclerosis, atherosclerosis, vascular hypertrophy associated with hypertension, hyperlipoproteinemia, normal vascular degeneration through aging, parathyroidal reactive hyperplasia, renal disease (e.g., acute or chronic), neoplastic diseases, inflammatory diseases, neurological and acute bronchopulmonary disease, tumorigenesis, ischemia-reperfusion syndrome, arthritis, sepsis, cognitive dysfunction, endotoxic shock, endotoxin-induced organ failure, and the like.

"Endothelial dysfunction" refers to the impaired ability in any physiological processes carried out by the endothelium, in particular, production of nitric oxide regardless of cause. It may be evaluated by, such as, for example, invasive techniques, such as, for example, coronary artery reactivity to acetylcholine or methacholine, and the like, or by noninvasive techniques, such as, for example, blood flow measurements, brachial artery flow dilation using cuff occlusion of the arm above or below the elbow, brachial artery ultrasonography, imaging techniques, measurement of circulating biomarkers, such as, asymmetric dimethylarginine (ADMA), and the like. For the latter measurement the endothelial-dependent flow-mediated dilation will be lower in patients diagnosed with an endothelial dysfunction.

"Methods for treating endothelial dysfunction" include, but are not limited to, treatment prior to the onset/diagnosis of a disease that is caused by or could result from endothelial dysfunction, such as, for example, atherosclerosis, hypertension, diabetes, heart failure, and the like.

"Methods for treating diseases caused by endothelial dysfunction" include, but are not limited to, the treatment of any disease resulting from the dysfunction of the endothelium, such as, for example, arteriosclerosis, heart failure, hypertension, cardiovascular diseases, cerebrovascular diseases, renovascular diseases, mesenteric vascular diseases, pulmonary vascular diseases, ocular vascular diseases, peripheral vascular diseases, peripheral ischemic diseases, and the like.

"Therapeutic agent" includes any therapeutic agent that can be used to treat or prevent the diseases described herein. "Therapeutic agents" include, for example, thrombolytic agents, antimicrobial compounds, antiproliferative agents, antisecretory agents, anti-cancer chemotherapeutic agents, steroids, immunosuppressive agents, radiotherapeutic agents, heavy metals functioning as a radiopaque agent, biologic agents, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, anti-thrombotic and vasodilator compounds, β-adrenergic antagonists, calcium channel blockers, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and the like. Therapeutic agent includes the pharmaceutically acceptable salts thereof, pro-drugs, and pharmaceutical derivatives thereof including, but not limited to, the corresponding nitrosated and/or nitrosylated and/or heterocyclic nitric oxide donor derivatives and/or nitroxide derivative. Although nitric oxide enhancing compounds have therapeutic activity, the term "therapeutic agent" does not include the nitric oxide enhancing compounds described herein, since nitric oxide enhancing compounds are separately defined.

"Prodrug" refers to a compound that is made more active in vivo.

"Antioxidant" refers to and includes any compound that can react and quench a free radical.

"Angiotensin converting enzyme (ACE) inhibitor" refers to compounds that inhibit an enzyme which catalyzes the conversion of angiotensin I to angiotensin II. ACE inhibitors include, but are not limited to, amino acids and derivatives thereof, peptides, including di- and tri-peptides, and antibodies to ACE which intervene in the renin-angiotensin system by inhibiting the activity of ACE thereby reducing or eliminating the formation of the pressor substance angiotensin II.

"Angiotensin II antagonists" refers to compounds which interfere with the function, synthesis or catabolism of angiotensin II. Angiotensin II antagonists include peptide compounds and non-peptide compounds, including, but not limited to, angiotensin II antagonists, angiotensin II receptor antagonists, agents that activate the catabolism of angiotensin II, and agents that prevent the synthesis of angiotensin I from angiotensin II. The renin-angiotensin system is involved in the regulation of hemodynamics and water and electrolyte balance. Factors that lower blood volume, renal perfusion pressure, or the concentration of sodium in plasma tend to activate the system, while factors that increase these parameters tend to suppress its function.

"Anti-hyperlipidemic compounds" refers to any compound or agent that has the effect of beneficially modifying serum cholesterol levels such as, for example, lowering serum low density lipoprotein (LDL) cholesterol levels, or inhibiting oxidation of LDL cholesterol, whereas high density lipoprotein (HDL) serum cholesterol levels may be lowered, remain the same, or be increased. Preferably, the anti-hyperlipidemic compound brings the serum levels of LDL cholesterol and HDL cholesterol (and, more preferably, triglyceride levels) to normal or nearly normal levels.

"Neutral endopeptidase inhibitors" refers to and includes compounds that are antagonists of the renin angiotensin aldosterone system including compounds that are dual inhibitors of neutral endopeptidases and angiotensin converting (ACE) enzymes.

"Renin inhibitors" refers to compounds which interfere with the activity of renin.

"Phosphodiesterase inhibitor" or "PDE inhibitor" refers to any compound that inhibits the enzyme phosphodiesterase. The term refers to selective or non-selective inhibitors of cyclic guanosine 3',5'-monophosphate phosphodiesterases (cGMP-PDE) and cyclic adenosine 3',5'-monophosphate phosphodiesterases (cAMP-PDE).

"Platelet reducing agents" refers to compounds that prevent the formation of a blood thrombus via any number of potential mechanisms. Platelet reducing agents include, but are not limited to, fibrinolytic agents, anti-coagulant agents and any inhibitors of platelet function. Inhibitors of platelet function include agents that impair the ability of mature platelets to perform their normal physiological roles (i.e., their normal function, such as, for example, adhesion to cellular and non-cellular entities, aggregation, release of factors such as growth factors) and the like.

"Proton pump inhibitor" refers to any compound that reversibly or irreversibly blocks gastric acid secretion by inhibiting the $H^+/K^+$-ATPase enzyme system at the secretory surface of the gastric parietal cell.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Cyclooxygenase-2 (COX-2) selective inhibitor" refers to a compound that selectively inhibits the cyclooxygenase-2 enzyme over the cyclooxygenase-1 enzyme. In one embodiment, the compound has a cyclooxygenase-2 $IC_{50}$ of less than about 2 µM and a cyclooxygenase-1 $IC_{50}$ of greater than about 5 µM, in the human whole blood COX-2 assay (as described in Brideau et al., *Inflamm Res.*, 45: 68-74 (1996)) and also has a selectivity ratio of cyclooxygenase-2 inhibition over cyclooxygenase-1 inhibition of at least 10, and preferably of at least 40. In another embodiment, the compound has a cyclooxygenase-1 $IC_{50}$ of greater than about 1 µM, and preferably of greater than 20 µM. The compound can also inhibit the enzyme, lipoxygenase. Such selectivity may indicate an ability to reduce the incidence of common NSAID-induced side effects.

"Patient" refers to animals, preferably mammals, most preferably humans, and includes males and females, and children and adults.

"Effective amount" refers to the amount of the compound and/or composition that is effective to achieve its intended purpose.

"Topical" refers to the delivery of a compound by application to the body surface and includes, but is not limited to, transdermal delivery and transmucosal delivery.

"Transdermal" refers to the delivery of a compound by passage through the skin and into the blood stream.

"Transmucosal" refers to delivery of a compound by passage of the compound through the mucosal tissue and into the blood stream.

"Parenteral" refers to delivery of a compound by subcutaneous, intravenous, intramuscular, intracardiac, intradermal, intraperitoneal, intrathecal or intrasternal injection and also includes infusion techniques.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Sustained release" refers to the release of an active compound and/or composition such that the blood levels of the active compound are maintained within a desirable therapeutic range over a period of time. The sustained release formulation can be prepared using any conventional method known to one skilled in the art to obtain the desired release characteristics.

"Nitric oxide enhancing" refers to compounds and functional groups which, under physiological conditions can increase endogenous nitric oxide. Nitric oxide enhancing compounds include, but are not limited to, nitric oxide releasing compounds, nitric oxide donating compounds, nitric oxide donors, radical scavenging compounds and/or reactive oxygen species scavenger compounds. In one embodiment the radical scavenging compound contains a nitroxide group.

"Nitroxide group" refers to compounds that have the ability to mimic superoxide dimutase and catalase and act as radical scavengers, or react with superoxide or other reactive oxygen species via a stable aminoxyl radical i.e. N-oxide.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, $NO·$), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, NO—, NO.), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo and/or are oxidized to produce nitric oxide and/or are substrates for nitric oxide synthase and/or cytochrome P450. "NO donor" also includes compounds that are precursors of L-arginine, inhibitors of the enzyme arginase and nitric oxide mediators.

"Heterocyclic nitric oxide donor" refers to a trisubstituted 5-membered ring comprising two or three nitrogen atoms and at least one oxygen atom. The heterocyclic nitric oxide donor is capable of donating and/or releasing a nitrogen monoxide species upon decomposition of the heterocyclic ring. Exemplary heterocyclic nitric oxide donors include oxatriazole-5-ones, oxatriazole-5-imines, sydnonimines, furoxans, and the like.

"Alkyl" refers to a lower alkyl group, a substituted lower alkyl group, a haloalkyl group, a hydroxyalkyl group, an alkenyl group, a substituted alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an ester, an amidyl, an oxo, a carboxyl, a carboxamido, a halo, a cyano, a nitrate, a nitrite, a thionitrate, a thionitrite or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$-$C_{10}$ hydrocarbon (preferably a $C_2$-$C_8$ hydrocarbon, more preferably a $C_2$-$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$-$C_4$ hydrocarbon that can comprise one or two carbon-carbon double bonds.

"Substituted alkenyl" refers to a branched or straight chain $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$-$C_{10}$ hydrocarbon (preferably a $C_2$-$C_8$ hydrocarbon, more preferably a $C_2$-$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronaphthyl, quinuclidyl, 2,6-dioxabicyclo(3.3.0)octane, 7-oxabicyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur may be in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamide nitrate and nitro. Exemplary heterocyclic groups include pyrrolyl, furyl, thienyl, 3-pyrrolinyl, 4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrahydrofuranyl, tetrazolyl, pyrrolinyl, pyrrolidinyl, oxazolidinyl 1,3-dioxolanyl, imidazolinyl, imidazolidinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl, 2,6-dioxabicyclo(3.3.0)octane, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinolyl, tetrahydronaphthyl, furanyl, indanyl, indenyl, indolyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbonyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$-$C_{10}$ hydrocarbon (preferably a $C_2$-$C_8$ hydrocarbon, more preferably a $C_2$-$C_6$ hydrocarbon) which can comprise one or more carbon-carbon double bonds.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkylheterocyclic ring" refers to a heterocyclic ring radical, as defined herein, attached to an alkyl radical, as defined herein. Exemplary alkylheterocyclic rings include 2-pyridylmethyl, 1-methylpiperidin-2-one-3-methyl, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Aryloxy" refers to $R_{55}O$—, wherein $R_{55}$ is an aryl group, as defined herein. Exemplary arylkoxy groups include naphthyloxy, quinolyloxy, isoquinolizinyloxy, and the like.

"Alkylthio" refers to $R_{50}S$—, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Arylalklythio" refers to an alkylthio group, as defined herein, to which is appended an aryl group, as defined herein. Exemplary arylalkylthio groups include benzylthio, phenylethylthio, chlorophenylethylthio, and the like.

"Arylalklythioalkyl" refers to an arylalkylthio group, as defined herein, to which is appended an alkyl group, as defined herein. Exemplary arylalkylthioalkyl groups include benzylthiomethyl, phenylethylthiomethyl, chlorophenylethylthioethyl, and the like.

"Alkylthioalkyl" refers to an alkylthio group, as defined herein, to which is appended an alkyl group, as defined herein. Exemplary alkylthioalkyl groups include alkylthiomethyl, ethylthiomethyl, trifluoroethylthiomethyl, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxy" refers to —O—

"Oxo" refers to =O.

"Oxylate" refers to —O⁻ $R_{77}^+$ wherein $R_{77}$ is an organic or inorganic cation.

"Thiol" refers to —SH.

"Thio" refers to —S—.

"Oxime" refers to =N—$OR_{81}$ wherein $R_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Hydrazone" refers to =N—N($R_{81}$)($R'_{81}$) wherein $R'_{81}$ is independently selected from $R_{81}$, and $R_{81}$ is as defined herein.

"Hydrazino" refers to $H_2N$—N(H)—.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, magnesium, calcium, and the like.

"Hydroxyalkyl" refers to a hydroxy group, as defined herein, appended to an alkyl group, as defined herein.

"Nitrate" refers to —O—$NO_2$ i.e. oxidized nitrogen.

"Nitrite" refers to —O—NO i.e. oxidized nitrogen.

"Thionitrate" refers to —S—$NO_2$.

"Thionitrite" and "nitrosothiol" refer to —S—NO.

"Nitro" refers to the group —$NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Imine" refers to —C(=N—$R_{51}$)— wherein $R_{51}$ is a hydrogen atom, an alkyl group, an aryl group or an arylheterocyclic ring, as defined herein "Amine" refers to any organic compound that contains at least one basic nitrogen atom.

"Amino" refers to —$NH_2$, an alkylamino group, a dialkylamino group, an arylamino group, a diarylamino group, an alkylarylamino group or a heterocyclic ring, as defined herein.

"Alkylamino" refers to $R_{50}$NH—, wherein $R_{50}$ is an alkyl group, as defined herein. Exemplary alkylamino groups include methylamino, ethylamino, butylamino, cyclohexylamino, and the like.

"Arylamino" refers to $R_{55}$NH—, wherein $R_{55}$ is an aryl group, as defined herein.

"Dialkylamino" refers to $R_{52}R_{53}$N—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}$N—, wherein $R_{55}$ and $R_{60}$ are each independently an aryl group, as defined herein.

"Alkylarylamino" or "arylalkylamino" refers to $R_{52}R_{55}$N—, wherein $R_{52}$ is an alkyl group, as defined herein, and $R_{55}$ is an aryl group, as defined herein.

"Alkylarylalkylamino" refers to $R_{52}R_{79}$N—, wherein $R_{52}$ is an alkyl group, as defined herein, and $R_{79}$ is an arylalkyl group, as defined herein.

"Alkylcycloalkylamino" refers to $R_{52}R_{80}$N—, wherein $R_{52}$ is an alkyl group, as defined herein, and $R_{80}$ is a cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, an arylamino group or an arylalkylamino group. Exemplary aminoaryl groups include anilino, N-methylanilino, N-benzylanilino, and the like.

"Thio" refers to —S—.

"Sulfinyl" refers to —S(O)—.

"Methanthial" refers to —C(S)—.

"Thial" refers to =S.

"Sulfonyl" refers to —$S(O)_2$—.

"Sulfonic acid" refers to —$S(O)_2OR_{76}$, wherein $R_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein "Sulfonic ester" refers to —$S(O)_2OR_{58}$, wherein $R_{58}$ is an alkyl group, an aryl group, or an aryl heterocyclic ring, as defined herein.

"Sulfonamido" refers to —$S(O)_2$—N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}$S—, wherein $R_{50}$ is an alkyl group, as defined herein (preferably a lower alkyl group, as defined herein).

"Arylthio" refers to $R_{55}$S—, wherein $R_{55}$ is an aryl group, as defined herein.

"Arylalkylthio" refers to an aryl group, as defined herein, appended to an alkylthio group, as defined herein.

"Alkylsulfinyl" refers to $R_{50}$—S(O)—, wherein $R_{50}$ is an alkyl group, as defined herein.

"Alkylsulfonyl" refers to $R_{50}$—$S(O)_2$—, wherein $R_{50}$ is an alkyl group, as defined herein.

"Alkylsulfonyloxy" refers to $R_{50}$—$S(O)_2$—O—, wherein $R_{50}$ is an alkyl group, as defined herein.

"Arylsulfinyl" refers to $R_{55}$—S(O)—, wherein $R_{55}$ is an aryl group, as defined herein.

"Arylsulfonyl" refers to $R_{55}$—$S(O)_2$—, wherein $R_{55}$ is an aryl group, as defined herein.

"Arylsulfonyloxy" refers to $R_{55}$—$S(O)_2$—O—, wherein $R_{55}$ is an aryl group, as defined herein.

"Amidyl" refers to $R_{51}$C(O)N($R_{57}$)— wherein $R_{51}$ and $R_{57}$ are each independently a hydrogen atom, an alkyl group, an aryl group or an arylheterocyclic ring, as defined herein.

"Ester" refers to $R_{51}$C(O)$R_{82}$— wherein $R_{51}$ is a hydrogen atom, an alkyl group, an aryl group or an arylheterocyclic ring, as defined herein and $R_{82}$ is oxygen or sulfur.

"Carbamoyl" refers to —O—C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)O$R_{76}$, wherein $R_{76}$ is a hydrogen, an organic cation or an inorganic cation, as defined herein.

"Carbonyl" refers to —C(O)—.

"Alkylcarbonyl" refers to $R_{52}$—C(O)—, wherein $R_{52}$ is an alkyl group, as defined herein.

"Arylcarbonyl" refers to $R_{55}$—C(O)—, wherein $R_{55}$ is an aryl group, as defined herein.

"Arylalkylcarbonyl" refers to $R_{55}$—$R_{52}$—C(O)—, wherein $R_{55}$ is an aryl group, as defined herein, and $R_{52}$ is an alkyl group, as defined herein.

"Alkylarylcarbonyl" refers to $R_{52}$—$R_{55}$—C(O)—, wherein $R_{55}$ is an aryl group, as defined herein, and $R_{52}$ is an alkyl group, as defined herein.

"Heterocyclicalkylcarbonyl" refer to $R_{78}$C(O)— wherein $R_{78}$ is a heterocyclicalkyl group, as defined herein.

"Carboxylic ester" refers to —C(O)O$R_{58}$, wherein $R_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Alkyl ester" refers to an alkyl group, as defined herein, appended to an ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Aryl ester" refers to an aryl group, as defined herein, appended to an ester group, as defined herein.

"Carboxamido" refers to —C(O)N($R_{51}$)($R_{57}$), wherein $R_{51}$ and $R_{57}$ are each independently a hydrogen atom, an alkyl group, an aryl group or an arylheterocyclic ring, as defined herein, or $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{59}$)—C(O)N($R_{51}$)($R_{57}$) wherein $R_{51}$, $R_{57}$, and $R_{59}$ are each independently a hydrogen atom, an alkyl group, an aryl group or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to —P($R_{70}$)($R_{71}$)($R_{72}$), wherein $R_{70}$ is a lone pair of electrons, thial or oxo, and $R_{71}$ and $R_{72}$ are each independently a covalent bond, a hydrogen, a lower alkyl, an alkoxy, an alkylamino, a hydroxy, an oxy or an aryl, as defined herein.

"Phosphoric acid" refers to —P(O)(O$R_{51}$)OH wherein $R_{51}$ is a hydrogen atom, an alkyl group, an aryl group or an arylheterocyclic ring, as defined herein.

"Phosphinic acid" refers to —P(O)($R_{51}$)OH wherein $R_{51}$ is a hydrogen atom, an alkyl group, an aryl group or an arylheterocyclic ring, as defined herein.

"Silyl" refers to —Si($R_{73}$)($R_{74}$)($R_{75}$), wherein $R_{73}$, $R_{74}$ and $R_{75}$ are each independently a covalent bond, a lower alkyl, an alkoxy, an aryl or an arylalkoxy, as defined herein.

"Organic acid" refers to compound having at least one carbon atom and one or more functional groups capable of releasing a proton to a basic group. The organic acid preferably contains a carboxyl, a sulfonic acid or a phosphoric acid moiety. Exemplary organic acids include acetic acid, benzoic acid, citric acid, camphorsulfonic acid, methanesulfonic acid, taurocholic acid, chlordronic acid, glyphosphate, medronic acid, and the like.

"Inorganic acid" refers to a compound that does not contain at least one carbon atom and is capable of releasing a proton to a basic group. Exemplary inorganic acids include hydrochloric acid, sulfuric acid, nitric acid, phosphoric acid, and the like.

"Organic base" refers to a carbon containing compound having one or more functional groups capable of accepting a proton from an acid group. The organic base preferably contains an amine group. Exemplary organic bases include triethylamine, benzyldiethylamine, dimethylethyl amine, imidazole, pyridine, pipyridine, and the like.

In another embodiment, the invention described furoxan compounds of Formula (I) or Formula (II) and pharmaceutically acceptable salts thereof:

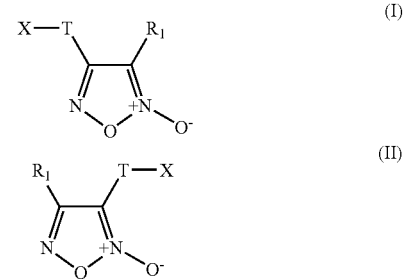

wherein:

$R_1$ is —$C_6H_4R_2$, —CN, —S(O)$_2C_6H_4R_2$, NO$_2$ or —C(O)—OR$_3$;

$R_2$ is hydrogen, —CN, —S(O)$_2R_3$, NO$_2$ or —C(O)—OR$_3$;

$R_3$ is an alkyl group or an aryl group;

T is a covalent bond, oxygen, S(O)$_o$ or NR$_4$;

o is an integer from 1 to 2;

$R_4$ is a hydrogen, a lower alkyl group or an aryl group;

X is —(CH$_2$)$_a$—N($R_5$)($R_6$), —(CHR$_7$)$_b$—CH$_2$-T-Z, —(CHR$_7$)$_b$—N($R_5$)($R_6$) or —CH$_2$—C(CH$_2$-T-Z)$_3$;

$R_5$ is a hydrogen, an alkyl group, an aryl group or —(CH$_2$)$_a$-T-Z;

$R_6$ is a hydrogen, an alkyl group, an aryl group, —(CH$_2$)$_a$-T-Z or —C(CH$_2$-T-Z)$_3$;

$R_7$ is hydrogen or -T-Z;

a is an integer from 2 to 5;

b is an integer from 1 to 6;

Z is

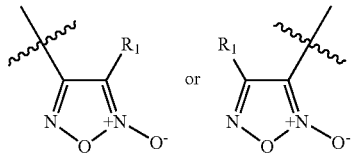

with the proviso that the furoxan compounds of Formula (I) and (II) must contain at least one Z group i.e. at least one furoxan moiety.

In cases where multiple designations of variables which reside in sequence are chosen as a "covalent bond" or the integer chosen is 0, the intent is to denote a single covalent bond connecting one radical to another. For example, $E_0$ would denote a covalent bond, while $E_2$ denotes (E-E) and $(C(R_4)(R_4))_2$ denotes —$C(R_4)(R_4)$—$C(R_4)(R_4)$—.

In other embodiments of the invention the compound of Formula (I) or Formula (II) is a compound containing two furoxan moieties, a compound containing three furoxan moieties and pharmaceutically acceptable salts thereof.

In another embodiment, the furoxan compound of Formula (I) or Formula (II) is: ethanamine, 2-[[5-oxido-4-(phenylsulfonyl)-1,2,5-oxadiazol-3-yl]oxy]-N,N-bis[2-[[5-oxido-4-(phenylsulfonyl)-1,2,5-oxadiazol-3-yl]oxy]ethyl]-; ethanamine, 2-[[5-oxido-4-(phenylsulfonyl)-1,2,5-oxadiazol-3-yl]oxy]-N-[2-[[5-oxido-4-(phenylsulfonyl)-1,2,5-oxadiazol-3-yl]oxy]ethyl]-; ethanol, 2-[bis[2-[[5-oxido-4-(phenylsulfonyl)-1,2,5-oxadiazol-3-yl]oxy]ethyl]amino]-; 1,2,5-oxadiazole, 3,3',3"-[1,2,3-propanetriyltris(oxy)]tris[4-(phenylsulfonyl)-, 5,5',5"-trioxide; 1,2,5-oxadiazole, 3,3'-[1,2-ethanediylbis(oxy)]bis[4-(phenylsulfonyl)-, 5,5'-dioxide; 1,2,5-oxadiazole-3-methanamine, 4-methyl-N-[(4-methyl-5-oxido-1,2,5, oxadiazol-3-yl)methyl]-, 5-oxide; and pharmaceutically acceptable salts thereof.

Compounds of the invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the invention anticipates and includes within its scope all such isomers and mixtures thereof.

Another embodiment of the invention describes the metabolites of the furoxan compounds and pharmaceutically acceptable salts thereof. These metabolites, include but are not limited to, the nitroxide compounds, degradation products, hydrolysis products, and the like, of the furoxan compounds and pharmaceutically acceptable salts thereof.

Another embodiment of the invention provides processes for making the novel compounds of the invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known for protecting thiol and alcohol groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application for the preparation of the compounds of this invention. The chemical reactions are described by, for example, Smith and March, *March's Advanced Organic Chemistry, Reactions, Mechanisms and Structure*, Fifth Edition, John Wiley & Sons, New York (2001) and by Larock, *Comprehensive Organic Transformations*, VCH Publishers, Inc. (1989). The compounds of the invention can be synthesized in a number of ways well known to one skilled in the art of organic synthesis. The compounds can be synthesized using the methods described herein, together with synthetic methods known in the art of synthetic organic chemistry, or by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials. Methods for the preparation of the compounds, include, but are not limited to, those described below. All references cited herein are hereby incorporated herein by reference in their entirety.

The compounds of Formulas (I) and (II) can be synthesized by one skilled in the art following the methods and examples described herein. The synthesis of the furoxan compounds containing only one furoxan moiety are also disclosed in, for example, U.S. Pat. No. 5,389,655, and in EP 0,574,726 A1, EP 0,581,062 A1, EP 0,683,159 A1; and in *Arzneim. Forsch. Drug Res.*, 47(11): 849-854 (1997); *Biochemical Pharmacol.*, 43: 1281-1288 (1992); *Bioorg & Med. Chem.*, 8: 1727-1732 (2000); *Bioorg & Med. Chem. Letts.*, 13: 4179-4186 (2003); *Br. J. Pharmacol.*, 114: 816-820 (1995); *Helv. Chim. Acta.*, 79: 1803-1817 (1996); *Il Farmaco*, 52: 339-341 (1997); *Il Farmaco*, 52: 405-410 (1997); *J. Heterocyclic Chem.*, 10: 587-590 (1973); *J. Heretocyclic Chem.*, 14:1415-1416 (1977); *J. Heterocyclic Chem.*, 33: 327-334 (1996); *J. Med. Chem.*, 35: 3296-3300 (1992); *J. Med. Chem.*, 38: 4944-4949 (1995); *J. Med. Chem.*, 37: 4412-4416 (1997); *J. Med. Chem.*, 40: 463-469 (1997); *J. Med. Chem.*, 41: 5393-5401 (1998); *J. Med. Chem.*, 42:1941-1950 (1999); *J. Med. Chem.*, 42:1422-1427 (1999); *J. Med. Chem.*, 44: 3463-3468 (2001); *J. Med. Chem.*, 46: 747-754 (2003); *J. Med. Chem.*, 46: 3762-3765 (2003); *J. Med. Chem.*, 47: 1840-1846 (2004); *J. Med. Chem.*, 47: 2688-2693 (2004); *Pharmaceutical Research*, 14: 1750-1758 (1997); *Pharmaceutical Res.* 18: 157-165 (2001); *Synthetic Comm.*, 1: 121-124 (1971); *Tet. Letts.*, 36: 3337-3340 (1995); the disclosures of each of which are incorporated by reference herein in their entirety. The furoxan compounds of the invention donate or transfer a biologically active form of nitrogen monoxide (i.e., nitric oxide).

Compounds contemplated for use of the invention, e.g., furoxan compounds that contain at lest two furoxan moieties, are, optionally, used in combination with nitric oxide enhancing compounds that release nitric oxide, increase endogeneous levels of nitric oxide or otherwise directly or indirectly deliver or transfer a biologically active form of nitrogen monoxide to a site of its intended activity, such as on a cell membrane in vivo.

Nitrogen monoxide can exist in three forms: NO— (nitroxyl), NO. (nitric oxide) and $NO^+$ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium ($NO^+$) does not react with $O_2$ or $O_2$— species, and functionalities capable of transferring and/or releasing $NO^+$ and NO— are also resistant to decomposition in the presence of many redox metals. Consequently, administration of charged NO equivalents (positive and/or negative) does not result in the generation of toxic by-products or the elimination of the active NO group.

The term "nitric oxide" encompasses uncharged nitric oxide (NO.) and charged nitrogen monoxide species, preferably charged nitrogen monoxide species, such as nitrosonium ion (NO+) and nitroxyl ion (NO—). The reactive form of nitric oxide can be provided by gaseous nitric oxide. The nitrogen monoxide releasing, delivering or transferring compounds have the structure F—NO, wherein F is a nitrogen monoxide releasing, delivering or transferring group, and include any and all such compounds which provide nitrogen monoxide to its intended site of action in a form active for its intended purpose.

The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-((2Z,3E)-4-ethyl-2-(hydroxyimino)-6-methyl-5-nitro-3-heptenyl)-3-pyridinecarboxamide (FR 146801), N-nitrosoamines, N-hydroxyl nitrosamines, nitrosimines, diazetine dioxides, oxatriazole 5-imines, oximes, hydroxylamines, N-hydroxyguanidines, hydroxyureas, benzofuroxanes, furoxans as well as substrates for the endogenous enzymes which synthesize nitric oxide.

Suitable NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio)butyl)-amino)diazen-1-ium-1,2-diolate (spermine NONOate or "SPER/NO") and sodium(Z)-(N,N-diethylamino)diazenium-1,2-diolate (diethylamine NONOate or "DEAJNO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

Suitable furoxanes include, but are not limited to, CAS 1609, C93-4759, C92-4678, S35b, CHF 2206, CHF 2363, and the like.

Suitable sydnonimines include, but are not limited to, molsidomine (N-ethoxycarbonyl-3-morpholinosydnonimine), SIN-1 (3-morpholinosydnonimine) CAS 936 (3-(cis-2,6-dimethylpiperidino)-N-(4-methoxybenzoyl)-sydnonimine, pirsidomine), C87-3754 (3-(cis-2,6-dimethylpiperidino)sydnonimine, linsidomine, C4144 (3-(3,3-dimethyl-1,4-thiazane-4-yl)sydnonimine hydrochloride), C89-4095 (3-(3,3-dimethyl-1,1-dioxo-1,4-thiazane-4-yl)sydnonimine hydrochloride, and the like.

Suitable oximes, include, but are not limited to, NOR-1, NOR-3, NOR-4, and the like.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5-200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3): 165-198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;

(ii) $ONS(C(R_e)(R_f))_m R_e$; or (iii) $H_2N$—$CH(CO_2H)$—$(CH_2)_n$, —$C(O)NH$—$CH(CH_2SNO)$—$C(O)NH$—$CH_2$—$CO_2H$, wherein m is an integer from 2 to 20;

$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalklythio, an arylalklythioalkyl, an alkylthioalkyl, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, —$U_3$—$V_5$, $V_6$, —$(C(R_o)(R_p))_{k1}$—$U_3$—$V_5$, —$(C(R_o)(R_p))_{k1}$—$U_3$—$V_6$, —$(C(R_o)(R_p))_k$—$U_3$—$C(O)$—$V_6$, or $R_e$ and $R_f$ taken together with the carbons to which they are attached form a carbonyl, a methanthial, a heterocyclic ring, a cycloalkyl group, an aryl group, an oxime, a hydrazone, a bridged cycloalkyl group,

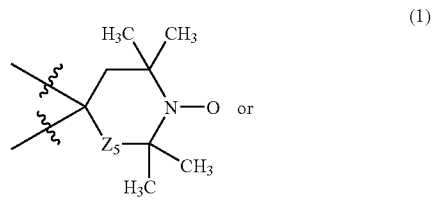

(1)

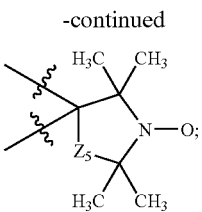
(2)

$R_o$ and $R_p$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, an arylalkylthio, an arylalkylthioalkyl, an alkylthioalkyl a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a sulfonic acid, a sulfonic ester, an alkylsulfonic acid, an arylsulfonic acid, an arylalkoxy, an alkylthio, an arylthio, a cyano, an aminoalkyl, an aminoaryl, an aryl, an arylalkyl, an alkylaryl, a carboxamido, an alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a sulfonamido, an alkylsulfonamido, an arylsulfonamido, an alkylsulfonyl, an alkylsulfonyloxy, an arylsulfonyl, arylsulphonyloxy, a sulfonic ester, an alkyl ester, an aryl ester, a urea, a phosphoryl, a nitro, —$U_3$—$V_5$, $V_6$, or $R_o$, and $R_p$ taken together with the carbons to which they are attached form a carbonyl, a methanthial, a heterocyclic ring, a cycloalkyl group, an aryl group, an oxime, an imine, a hydrazone, a bridged cycloalkyl group,

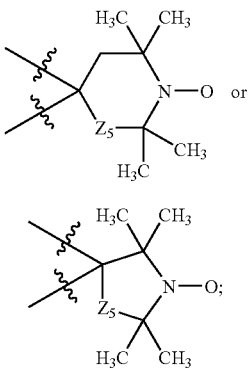
(1)

(2)

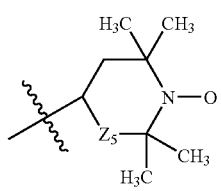
(1)

$k_1$ is an integer form 1 to 3;
$U_3$ is an oxygen, sulfur- or —$N(R_a)R_i$;
$V_5$ is —NO or —$NO_2$ (i.e. an oxidized nitrogen);
$V_6$ is:

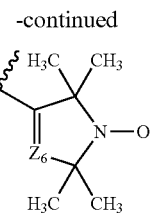
(2)

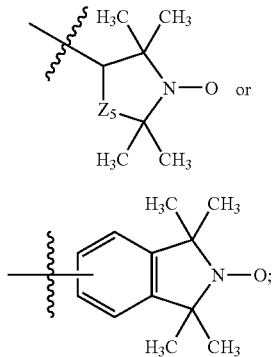
(3)

(4)

$Z_5$ is —$CH_2$ or oxygen;
$Z_6$ is —CH or nitrogen;
$R_a$ is a lone pair of electrons, a hydrogen or an alkyl group;
$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, —$CH_2$—$C(U_3$—$V_5)(R_e)(R_f)$, a bond to an adjacent atom creating a double bond to that atom or —($N_2O_2$—)—·$M_1^+$, wherein $M_1^+$ is an organic or inorganic cation.

In cases where $R_e$ and $R_f$ are independently a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the invention, where the NO adduct is a compound that donates, transfers or releases nitric oxide, include compounds comprising at least one ON—O— or ON—N— group. The compounds that include at least one ON—O— or ON—N— group are preferably ON—O— or ON—N— polypeptides (the term "polypeptide" includes proteins and polyamino acids that do not possess an ascertained biological function, and derivatives thereof); ON—O— or ON—N— amino acids (including natural and synthetic amino acids and their stereoisomers and racemic mixtures); ON—O— or ON—N— sugars; ON—O— or —ON—N— modified or unmodified oligonucleotides (comprising at least 5 nucleotides, preferably 5-200 nucleotides); ON—O— or ON—N— straight or branched, saturated or unsaturated, aliphatic or aromatic, substituted or unsubstituted hydrocarbons; and ON—O—, ON—N— or ON—C— heterocyclic compounds. Examples of compounds comprising at least one ON—O— or ON—N— group include butyl nitrite, isobutyl nitrite, tert-butyl nitrite, amyl nitrite, isoamyl nitrite, N-nitrosamines, N-nitrosamides, N-nitrosourea, N-nitrosoguanidines, N-nitrosocarbamates, N-acyl-N-nitroso compounds (such as, N-methyl-N-nitrosourea); N-hydroxy-N-nitrosamines, cupferron, alanosine, dopastin, 1,3-disubstitued nitrosiminobenzimidazoles, 1,3,4-thiadiazole-2-nitrosimines, benzothiazole-2(3H)-nitrosimines, thiazole-2-nitrosimines, oligonitroso sydnonimines, 3-alkyl-N-nitroso-sydnonimines, 2H-1,3,4-thiadiazine nitrosimines.

Another group of NO adducts for use in the invention include nitrates that donate, transfer or release nitric oxide, such as compounds comprising at least one $O_2N$—O—, $O_2N$—N— or $O_2N$—S— group. Among these compounds are $O_2N$—O—, $O_2N$—N— or $O_2N$—S— polypeptides (the term "polypeptide" includes proteins and also polyamino acids that do not possess an ascertained biological function, and derivatives thereof); $O_2N$—O—, $O_2N$—N— or $O_2N$—S— amino acids (including natural and synthetic amino acids and their stereoisomers and racemic mixtures); $O_2N$—O—, $O_2N$—N— or $O_2N$—S— sugars; $O_2N$—O—, $O_2N$—N— or $O_2N$—S— modified and unmodified oligonucleotides (comprising at least 5 nucleotides, preferably 5-200 nucleotides); $O_2N$—O—, $O_2N$—N— or $O_2N$—S— straight or branched, saturated or unsaturated, aliphatic or aromatic, substituted or unsubstituted hydrocarbons; and $O_2N$—O—, $O_2N$—N— or $O_2N$—S— heterocyclic compounds. Examples of compounds comprising at least one $O_2N$—O—, $O_2N$—N— or $O_2N$—S— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 4757, SPM 5185, SPM 5186 and those disclosed in U.S. Pat. Nos. 5,284,872, 5,428,061, 5,661,129, 5,807,847 and 5,883,122 and in WO 97/46521, WO 00/54756 and in WO 03/013432, the disclosures of each of which are incorporated by reference herein in their entirety.

Another group of NO adducts are N-oxo-N-nitrosoamines that donate, transfer or release nitric oxide and are represented by the formula: $R^{1''}R^{2''}N$—N(O-$M^+$)—NO, where $R^{1''}$ and $R^{2''}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M_1^+$ is an organic or inorganic cation, such as for example, an alkyl substituted ammonium cation or a Group I metal cation.

The invention is also directed to compounds that stimulate endogenous NO or elevate levels of endogenous endothelium-derived relaxing factor (EDRF) in vivo or are oxidized to produce nitric oxide and/or are substrates for nitric oxide synthase and/or cytochrome P450. Such compounds include, for example, L-arginine, L-homoarginine, and N-hydroxy-L-arginine, N-hydroxy-L-homoarginine, N-hydroxydebrisoquine, N-hydroxypentamidine including their nitrosated and/or nitrosylated analogs (e.g., nitrosated L-arginine, nitrosylated L-arginine, nitrosated N-hydroxy-L-arginine, nitrosylated N-hydroxy-L-arginine, nitrosated and nitrosylated L-homoarginine), N-hydroxyguanidine compounds, amidoxime, ketoximes, aldoxime compounds, that can be oxidized in vivo to produce nitric oxide. Compounds that may be substrates for a cytochrome P450, include, for example, imino(benzylamino)methylhydroxylamine, imino(((4-methylphenyl)methyl)amino)methylhydroxylamine, imino(((4-methoxyphenyl)methyl)amino)methylhydroxylamine, imino(((4-(trifluoromethyl)phenyl)methyl)amino)methylhydroxylamine, imino(((4-nitrophenyl)methyl)amino)methylhydroxylamine, (butylamino)iminomethylhydroxylamine, imino (propylamino)methylhydroxylamine, imino(pentylamino)methylhydroxylamine, imino (propylamino)methylhydroxylamine, imino ((methylethyl)amino)methylhydroxylamine, (cyclopropylamino)iminomethylhydroxylamine, imino-2-1,2,3,4-tetrahydroisoquinolyl methylhydroxylamine, imino(1-methyl(2-1,2,3,4-tetrahydroisoquinolyl))methylhydroxylamine, (1,3-dimethyl(2-1,2,3,4-tetrahydroisoquinolyl))iminomethylhydroxylamine, (((4-chlorophenyl)methyl)amino)iminomethylhydroxylamine, ((4-chlorophenyl)amino)iminomethylhydroxylamine, (4-chlorophenyl)(hydroxyimino)methylamine, and 1-(4-chlorophenyl)-1-(hydroxyimino)ethane, and the like, precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid), nitric oxide mediators and/or physiologically acceptable salts thereof, including, for example, pyruvate, pyruvate precursors, α-keto acids having four or more carbon atoms, precursors of α-keto acids having four or more carbon atoms (as disclosed in WO 03/017996, the disclosure of which is incorporated herein in its entirety), and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524-526 (1987); Ignarro et al, *Proc. Natl. Acad. Sci. USA*, 84:9265-9269 (1987)).

The invention is also directed to nitric oxide enhancing compounds that can increase endogenous nitric oxide. Such compounds, include for example, nitroxide containing compounds, include, but are not limited to, substituted 2,2,6,6-tetramethyl-1-piperidinyloxy compounds, substituted 2,2,5,5-tetramethyl-3-pyrroline-1-oxyl compounds, substituted 2,2,5,5-tetramethyl-1-pyrrolidinyloxy compounds, substituted 1,1,3,3-tetramethylisoindolin-2-yloxyl compounds, substituted 2,2,4,4-tetramethyl-1-oxazolidinyl-3-oxyl compounds, substituted 3-imidazolin-1-yloxy, 2,2,5,5-tetramethyl-3-imidazolin-1-yloxyl compounds, OT-551, 4-hydroxy-2,2,6,6-tetramethyl-1-piperidinyloxy (tempol), and the like. Suitable substituents, include, but are not limited to, aminomethyl, benzoyl, 2-bromoacetamido, 2-(2-(2-bromoacetamido)ethoxy)ethylcarbamoyl, carbamoyl, carboxy, cyano, 5-(dimethylamino)-1-naphthalenesulfonamido, ethoxyfluorophosphinyloxy, ethyl, 5-fluoro-2,4-dinitroanilino, hydroxy, 2-iodoacetamido, isothiocyanato, isothiocyanatomethyl, methyl, maleimido, maleimidoethyl, 2-(2-maleimidoethoxy)ethylcarbamoyl, maleimidomethyl, maleimido, oxo, phosphonooxy, and the like.

The invention is also based on the discovery that compounds and compositions of the invention may be used in conjunction with other therapeutic agents for co-therapies, partially or completely, in place of other therapeutic agents, such as, for example, thrombolytic agents, antimicrobial compounds, antiproliferative agents, antisecretory agents, anti-cancer chemotherapeutic agents, steroids, immunosuppressive agents, radiotherapeutic agents, heavy metals functioning as a radiopaque agent, biologic agents, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, endothelin antagonists, hydralazine compounds, $H_2$ receptor antagonists, neutral endopeptidase inhibitors, non-steroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. The therapeutic agent may optionally be nitrosated and/or nitrosylated and/or contain at least one heterocyclic nitric oxide donor group and/or at least one nitroxide group.

Suitable thrombolytic agents, include, but are not limited to, urokinase, streptokinase, tissue plasminogen activators, and the like.

Suitable antimicrobial compounds, include, but are not limited to, acediasulfone, aceturate, acetyl sulfametossipirazine, acetyl sulfamethoxypyrazine, acranil, albendazole, alexidine, amatadine, ambazone, amdinocillin, amikacin, p-aminosalicylic acid, p-aminosalicylic acid hydrazine, amoxicillin, ampicillin, anisomycin, apalcillin, apicyclin, apramycin, arbekacin, argininsa, aspoxicillin, azidamfenicol, azidocillin, azithromycin, azlocillin, aztreonam, bacampicillin, bacitracin, benzoylpas, benzyl penicillin acid, benzyl sulfamide, bicozamycin, bipenam, brodimoprim, capreomycin, carbenicillin, carbomycin, cafazedone, carindacillin, carumonam, cefcapene pivoxil, cefaclor, cefadroxil, cefafroxil, cefamandole, cefatamet, cefatrizine, cefazedone, cefazolin, cefbuperazone, cefclidin, cefdinir, cefditoren, cefixime, cefmenoxime, cefmetazole, cefminox, cefodizime, cefonicid, cefoperazone, ceforanide, cefotaxime, cefotetan, cefotiam, cefoxitin, cefozopran, cefpimizole, cefpiramide, cefpirome, cefpodoxime proxetil, cefprozil, cefroxadine, cefsulodin, ceftazidime, cefteram, ceftezole, ceftibuten, ceftiofur, ceftizoxime, ceftriaxone, cefuroxime, cefuzonam, cephacetrile sodium, cephadrine, cephalexin, cephaloglycin, cephaloridine, cephalosporin C, cephalothin, cephapirin sodium, cephradine, chibrorifamycin, chloramphenicol, chlorotetracycline, cinoxacin, ciprofloxacin, claritromycin, clavulanic acid, clinafloxacin, clindamycin, clofazimine, clofoctal, clometocillin, clomocycline, cloxacillin, cloxyquin, colistin, cyclacilline, cycloserine, danoflaxcin, dapsone, deoxycycline, deoxydihydrostreptomycin, dibekacin, dicloxacillin, difloxacin, dihydrostreptomycin, dimetridazole, diminazene, dirirtomycin, duramycin, eflornithine, enrofloxacin, enviomycin, epicillin, erythromycin, etacillin, ethambutol, ethionamide, famcyclovir, fenbecillin, fleroxacin, flomoxef, floxacillin, flumequine, n-formamidoylthienamycin, furonazide, fortimycin, furazolium chloride, gentamycin, glyconiazide, gramicidin, grepafloxacin, guamecycline, halofuginone, hetacillin, homidium, hydroxyl-stilbamidine, ibostamycin, imidocarb, imipenam, ipronidazole, isoniazide, josamycin, inosine, kanamycin, lauroguadine, lenampicillin, lincomycin, lomefloxacin, loracarbef, lymecycline, mafenide, mebendazole, meclocyclin, meropenem, metampicillin, metacicline, methacycline, methicillin sodium, metronidazole, 4'-(methylsulfamoyl)sulfanilanilide, mezlocillin, meziocillin, micronomycin, midecamycin $A_1$, minocycline, miocamycin, miokamycin, morfazinamide, moxalactam, mupirocin, myxin, nadifloxacin, nalidixic acid, negamycin, neomycin, netlimycin, nifurfoline, nifurpirinol, nifurprazine, nimorazole, nitroxoline, norfloxacin, novobiocin, ofloxacin, oleandomycin, opiniazide, oxacillin, oxophenarsine, oxolinic acid, oxytetracycline, panipenam, paromycin, pazufloxacin, pefloxacin, penicillin G potassium salt, penicillin N, penicillin O, penicillin V, penethamate hydroiodide, pentamidine, phenamidine, phenethicillin potassium salt, phenyl aminosalicylate, pipacycline, pipemidic acid, piperacillin, pirlimycin, piromidic acid, pivampicillin, pivcefalexin, polymyxin B, porfiromycin, propamidine, propicillin, protionamide, puraltadone, puromycin, pyrazinamide, pyrimethamine, quinacillin, quinacrine, quinapyramine, quintine, ribostamycin, rifabutin, rifamide, rifampin, rifamycin, rifanpin, rifapentine, rifaxymine, ritipenem, rokitamycin, rolitetracycline, rosamycin, rufloxacin, salazosulfadimidine, salinazid, sancycline, sarafloxacin, sedacamycin, secnidazole, sisomycin, sparfloxacin, spectinomycin, spiramycin, spiramycin I, spiramycin II, spiramycin III, stilbamidine, streptomycin, streptonicizid, sulbactam, sulbenicillin, succisulfone, sulfanilamide, sulfabenzamide, sulfacetamide, sulfachloropyridazine, sulfachrysoidine, sulfacytine, sulfadiazine, sulfadicramide, sulfadimethoxine, sulfadoxine, sulfadrazine, sulfaetidol, sulfafenazol, sulfaguanidine, sulfaguanole, sulfalene, sulfamerazine, sulfameter, sulfamethazine, sulfamethizole, sulfamethomidine, sulfamethoxazole, sulfamethoxypyridazine, sulfamethylthiazol, sulfamethylthiazole, sulfametrole, sulfamidochrysoidine, sulfamoxole, sulfanilamide, 4-sulfanilamido salicylic acid, 4-4'-sulfanilylbenzylamine, p-sulfanilylbenzylamine, 2-p-sulfinylanilinoethanol, sulfanilylurea, sulfoniazide, sulfaperine, sulfaphenazole, sulfaproxyline, sulfapyrazine, sulfapyridine, sulfathiazole, sulfaethidole, sulfathiourea, sulfisomidine, sulfasomizole, sulfasymazine, sulfisoxazole, 4,4'-sulfinyldianiline, $N^4$-sulfanilylsulfanilamide, N-sulfanilyl-3,4-xylamide, sultamicillin, talampicillin, tambutol, taurolidine, teiclplanin, temocillin, tetracycline, tetroxoprim, thiabendazole, thiazolsulfone, tibezonium iodide, ticarcillin, tigemonam, tinidazole, tobramycin, tosufloxacin, trimethoprim, troleandromycin, trospectomycin, trovafloxacin, tubercidine, miokamycin, oleandomycin, troleandromycin, vancomycin, verazide, viomycin, virginiamycin, zalcitabine, PA-1806 and PA-2794, and the like. Suitable antimicrobial compounds are described more fully in the literature, such as in Goodman and Gilman, The Pharmacological Basis of Therapeutics (9th Edition), McGraw-Hill, (1996); Merck Index on CD-ROM, $13^{th}$ Edition; STN Express, file phar and file registry, the disclosures of each of which are incorporated by reference herein in their entirety.

In some embodiments the antimicrobial compound amikacin, azithromycin, azetreonam, bacitracin, carbenicillin, cefazolin, cefoxitin, cephaloridine, chibrorifamycin, chloramphenicol, colistin, duramycin, n-formamidoylthienamycin, gentamycin, gramicidin, kanamycin, neomycin, penicillin G, polymyxin B, sisomicin, tetracyclines, tigecycline, tobramycin, vancomycin, PA-1806 and PA-2794.

In other embodiments the antimicrobial compound is an antiviral compound, including but not limited to, acyclovir, amatadine, cidofovir, cytarabine, didanosine, dideoxyadenosine, edoxudine, famciclovir, floxuridine, gancyclovir, idoxuridine, indanavir, kethoxal, lamivudine, MADU, penciclovir, podophyllotoxin, ribavirin, rimantadine, saquinavir, sorivudine, stavudine, trifluridine, valcyclovir, vidarabine, xenazoic acid, zalcitabine, zidovudine, and the like.

Suitable antiproliferative agents, include, but are not limited to, colchicine, methotrexate, azathioprine, vincristine, vinblastine, cytochalasin, fluorouracil, adriamycin, mutamycin, tubercidin, epothilone A or B, discodermolide, taxol, taxane compounds, and the like.

Suitable antisecretory agents, include, but are not limited to, retinoid, retinoic acid, and the like.

Suitable anti-cancer agents, include, bit are not limited to, tamoxifen citrate, acivicin, bizelesin, daunorubicin, epirubicin, mitoxantrone, and the like.

Suitable steroids include, but are not limited to, 21-acetoxypregnenolone, alcolometasone, algestone, amcinonide, beclomethasone, betamethasone, budesonide, chlorprednisone, clobetasol, clobentasone, clocortolone, cloprednol, corticosterone, cortisine, corticazol (cortivatol), deflazacort, desonide, desoximetasone, dexamethasone, diflorasone, diflucortolone, difluprednate, enoxolone, fluzacort, flucloronide, flumethasone, flunisolide, flucinolone acetonide, fluocininide, fluocortin butyl, fluocortolone, fluorometholone, fluperolone acetate, fluprednidene acetate, fluprednisolone, flurandrenolide, fluticasone propionate, fluticasone propionate, formocortal, halcinonide, halobetasol propionate, halometasone, haloprednone acetate, hydrocortamate, hydrocortisone and its derivatives (such as phosphate, 21-sodium succinate and the like), hydrocortisone terbutate, isoflupredone, loteprednol etabonate, mazipredone, medrysone, meprednisone, methylprednisolone, mometasone furoate, paremethasone, prednicarbate, prednisolone and its derivatives (such as 21-stearoylglycolate, sodium phosphate and the like), prednisone, prednival, prednylidene and its derivatives (such as 21-diethylaminoactetate and the like), rimexolone, tixocortol, trimcinolone and its derivatives (such as acetonide, benetonide and the like), and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, 13$^{th}$ Edition; and in U.S. Pat. Nos. 6,057,347 and 6,297,260 assigned to NitroMed. Inc., the disclosures of which are incorporated herein by reference in their entirety.

In some embodiments the steroids are dexamethasone, fluorometholone, hydrocortisone, and prednisolone.

Suitable immunosuppressive agents, include, but are not limited to, cyclosporin, rapamycin, and the like.

Suitable radiotherapeutic agents, include, but are not limited to, $^{60}$Co (5.3 year half life), $^{192}$Ir (73.8 days), $^{32}$P (14.3 days), $^{111}$In (68 hours), $^{90}$Y (64 hours), $^{99m}$Tc (6 hours), and the like.

Suitable heavy metals functioning as radiopaque agents, include, but are not limited to, iodine-containing compounds, barium-containing compounds, gold, tantalum, platinum, tungsten, and the like.

Suitable biologic agents, include, but are not limited to, peptides, proteins, enzymes, extracellular matrix components, cellular components, and the like.

Suitable aldosterone antagonists include, but are not limited to, canrenone, potassium canrenoate, drospirenone, spironolactone, eplernone (INSPRA®), epoxymexrenone, fadrozole, pregn-4-ene-7,2,1-dicarboxylic acid, 9,11-epoxy-17-hydroxy-3-oxo, γ-lactone, methyl ester, (7α,11α,17β.)-; pregn-4-ene-7,21-dicarboxylic acid, 9,11-epoxy-17-hydroxy-3-oxo-dimethyl ester, (7α,11α,17β.)-; 3'H-cyclopropa(6,7)pregna-4,6-diene-21-carboxylic acid, 9,11-epoxy-6,7-dihydro-17-hydroxy-3-oxo-, γ-lactone, (6β,7β,17β)-; pregn-4-ene-7,21-dicarboxylic acid, 9,11-epoxy-17-hydroxy-3-oxo-, 7-(1-methylethyl)ester, monopotassium salt, (7α,11α,17β.)-; pregn-4-ene-7,21-dicarboxylic acid, 9,11,-epoxy-17-hydroxy-3-oxo-, 7-methyl ester, monopotassium salt, (7α,11α,17β.)-; 3'H-cyclopropa(6,7) pregna-1,4,6-triene-21-carboxylic acid, 9,11-epoxy-6,7-dihydro-17-hydroxy-3-oxo-, γ-lactone, (6β,7β,11α)-; 3'H-cyclopropa(6,7)pregna-4,6-diene-21-carboxylic acid, 9,11-epoxy-6,7-dihydro-17-hydroxy-3-oxo-, methyl ester, (6β,7β,11α,17β)-; 3'H-cyclopropa (6,7)pregna-4,6-diene-21-carboxylic acid, 9,11-epoxy-6,7-dihydro-17-hydroxy-3-oxo-, monopotassium salt, (6β,7β,11α,17β)-; 3'H-cyclopropa(6,7)pregna-1,4,6-triene-21-carboxylic acid, 9,11-epoxy-6,7-dihydro-17-hydroxy-3-oxo-, γ-lactone, (6β,7β,11α,17β)-; pregn-4-ene-7,21-dicarboxylic acid, 9,11-epoxy-17-hydroxy-3-oxo-, γ-lactone, ethyl ester, (7α,11α,17β)-; pregn-4-ene-7,21-dicarboxylic acid, 9,11-epoxy-17-hydroxy-3-oxo-, γ-lactone, 1-methylethyl ester, (7α,11α,17β)-; RU-28318, and the like. One skilled in the art will appreciate that the aldosterone antagonists can be administered in the form of their pharmaceutically acceptable salts and/or stereoisomers. Suitable aldosterone antagonists are described more fully in the literature, such as in Goodman and Gilman, The Pharmacological Basis of Therapeutics (9th Edition), McGraw-Hill, 1995; and the Merck Index on CD-ROM, 13$^{th}$ Edition; and on STN Express, file phar and file registry.

In some embodiments, the aldosterone antagonist is eplernone or spironolactone (a potassium sparing diuretic that acts like an aldosterone antagonist). In one embodiment eplernone is administered in an amount of about 25 milligrams to about 300 milligrams as a single dose or as multiple doses per day; the spironolactone is administered in an amount of about 25 milligrams to about 150 milligrams as a single dose or as multiple doses per day.

Suitable alpha-adrenergic receptor antagonists include but are not limited to, phentolamine, tolazoline, idazoxan, deriglidole, RX 821002, BRL 44408, BRL 44409, BAM 1303, labetelol, ifenprodil, rauwolscine, corynathine, raubascine, tetrahydroalstonine, apoyohimbine, akuarnmigine, β-yohimbine, yohimbol, yohimbine, pseudoyohimbine, epi-3α-yohimbine, 10-hydroxy-yohimbine, 11-hydroxy-yohimbine, tamsulosin, benoxathian, atipamezole, BE 2254, WB 4101, HU-723, tedisamil, mirtazipine, setiptiline, reboxitine, delequamine, naftopil, saterinone, SL 89.0591, ARC 239, urapidil, 5-methylurapidil, monatepi, haloperidol, indoramin, SB 216469, moxisylyte, trazodone, dapiprozole, efaroxan, Recordati 15/2739, SNAP 1069, SNAP 5089, SNAP 5272, RS 17053, SL 89.0591, KMD 3213, spiperone, AH 11110A, chloroethylclonidine, BMY 7378, niguldipine, and the like. Suitable alpha-adrenergic receptor antagonists are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable angiotensin II antagonists include, but are not limited to, angiotensin, abitesartan, candesartan, candesartan cilexetil, elisartan, embusartan, enoltasosartan, eprosartan, fonsartan, forasartan, glycyllosartan, irbesartan, losartan, olmesartan, milfasartan, medoxomil, ripisartan, pratosartan, saprisartan, saralasin, sarmesin, tasosartan, temisartan, valsartan, zolasartan, 3-(2'(tetrazole-5-yl)-1,1'-biphen-4-yl)methyl-5,7-dimethyl-2-ethyl-3H-imidazo[4,5-b]pyridine, antibodies to angiotensin II, A-81282, A-81988, BAY 106734, BIBR-363, BIBS-39, BIBS-222, BMS-180560, BMS-184698, BMS-346567, CGP-38560A, CGP-42112A, CGP-48369, CGP-49870, CGP-63170, CI-996, CP-148130, CL-329167, CV-11194, DA-2079, DE-3489, DMP-811, DuP-167, DuP-532, DuP-753, E-1477, E-4177, E-4188, EMD-66397, EMD-666R4, EMD-73495, EMD-66684, EXP-063, EXP-929, EXP-3174, EXP-6155, EXP-6803, EXP-7711, EXP-9270, EXP-9954, FK-739, FRI 153332, GA-0050, GA-0056, HN-65021, HOE-720, HR-720, ICI-D6888, ICI-D7155, ICI-D8731, KRI-1177, KT3-671, KT-3579, KW-3433, L-158809, L-158978, L-159282, L-159689, L-159874, L-161177, L-162154, L-162234, L-162441, L-163017, L-163017, LF-70156, LRB-057, LRB-081, LRB-087, LY-235656, LY-266099, LY-285434, LY-301875, LY-302289, LY-315995, ME-3221, MK-954, PD-123177, PD-123319, PD-126055, PD-150304, RG-13647, RWJ-38970, RWJ-46458, S-8307, S-8308, SC-51757, SC-54629, SC-52458, SC-52459, SK 1080, SL-910102, SR-47436, TAK-536, UP-2696, U-96849, U-97018, UK-77778, UP-275-22, WAY-126227, WK-1260, WK-1360, WK-1492, WY 126227, YH-1498, YM-358, YM-31472, X-6803, XH-148, XR-510, ZD-6888, ZD-7155, ZD-8731, ZD 8131, the compounds of ACS registry numbers 124750-92-1, 133240-46-7, 135070-05-2, 139958-16-0, 145160-84-5, 147403-03-0, 153806-29-2, 439904-54-8P, 439904-55-9P, 439904-56-0P, 439904-57-1P, 439904-58-2P, 155918-60-8P, 155918-61-9P, 272438-16-1P, 272446-75-0P, 223926-77-0P, 169281-89-4, 439904-65-1P, 165113-01-9P, 165113-02-0P, 165113-03-1P, 165113-03-2P, 165113-05-3P, 165113-06-4P, 165113-07-5P, 165113-08-6P, 165113-09-7P, 165113-10-0P, 165113-11-IP, 165113-12-2P, 165113-17-7P, 165113-18-8P, 165113-19-9P, 165113-20-2P, 165113-13-3P, 165113-14-4P, 165113-15-5P, 165113-16-6P, 165113-21-3P, 165113-22-4P, 165113-23-SP, 165113-24-6P, 165113-25-7P, 165113-26-8P, 165113-27-9P, 165113-28-0P, 165113-29-1P, 165113-30-4P, 165113-31-SP, 165113-32-6P, 165113-33-7P, 165113-34-8P, 165113-35-9P, 165113-36-0P, 165113-37-1P, 165113-38-2P, 165113-39-3P, 165113-40-6P, 165113-41-7P, 165113-42-8P, 165113-43-9P, 165113-44-0P, 165113-45-1P, 165113-46-2P, 165113-47-3P, 165113-48-4P, 165113-49-5P, 165113-50-8P, 165113-51-9P, 165113-52-0P, 165113-53-1P, 165113-54-2P, 165113-55-3P, 165113-56-4P, 165113-57-5P, 165113-58-6P, 165113-59-7P, 165113-60-0P, 165113-61-1P, 165113-62-2P, 165113-63-3P, 165113-64-4P, 165113-65-5P, 165113-66-6P, 165113-67-7P, 165113-68-8P, 165113-69-9P, 165113-70-2P, 165113-71-3P, 165113-72-4P, 165113-73-5P, 165113-74-6P, 114798-27-5, 114798-28-6, 114798-29-7, 124749-82-2, 114798-28-6, 124749-84-4, 124750-88-5, 124750-91-0, 124750-93-2, 161946-65-2P, 161947-47-3P, 161947-48-4P, 161947-51-9P, 161947-52-0P, 161947-55-3P, 161947-56-4P, 161947-60-0P, 161947-61-1P, 161947-68-8P, 161947-69-9P, 161947-70-2P, 161947-71-3P, 161947-72-4P, 161947-74-6P, 161947-75-7P, 161947-81-5P, 161947-82-6P, 161947-83-7P, 161947-84-8P, 161947-85-9P, 161947-86-0P, 161947-87-1P, 161947-88-2P, 161947-89-3P, 161947-90-6P, 161947-91-7P, 161947-92-8P, 161947-93-9P, 161947-94-0P, 161947-95-1P, 161947-96-2P, 161947-97-3P, 161947-98-4P, 161947-99-5P, 161948-00-1P, 161948-01-2P, 161948-02-3P, 168686-32-6P, 167301-42-0P, 166813-82-7P, 166961-56-4P, 166961-58-6P, 158872-96-9P, 158872-97-0P, 158807-14-8P, 158807-15-9P, 158807-16-0P, 158807-17-1P, 158807-18-2P, 158807-19-3P, 158807-20-6P, 155884-08-5P, 154749-99-2, 167371-59-7P, 244126-99-6P, 177848-35-0P and 141309-82-2P, and the like. One skilled in the art will appreciate that the angiotensin II antagonists can be administered in the form of pharmaceutically acceptable salts and/or stereoisomers. Suitable angiotensin II antagonists are described more fully in the literature, such as in Goodman and Gilman, The Pharmacological Basis of Therapeutics (9th Edition), McGraw-Hill, 1995; and the Merck Index on CD-ROM, 13th Edition; and on STN Express, file phar and file registry.

In one embodiment the angiotensin II antagonists are candesartan, eprosartan, irbesartan, losartan, omlesartan, telmisartan or valsartan. In other embodiments the candesartan is administered as candesartan cilexetil in an amount of about 15 milligrams to about 100 milligrams as a single dose or as multiple doses per day; the eprosartan is administered as eprosartan mesylate in an amount of about 400 milligrams to about 1600 milligrams as a single dose or as multiple doses per day; the irbesartan is administered in an amount of about 75 milligrams to about 1200 milligrams as a single dose or as multiple doses per day; the losartan is administered as losartan potassium in an amount of about 25 milligrams to about 100 milligrams as a single dose or as multiple doses per day; the omlesartan is administered as omlesartan medoxomil in an amount of about 5 milligrams to about 40 milligrams as a single dose or as multiple doses per day; the telmisartan is administered in an amount of about 20 milligrams to about 80 milligrams as a single dose or as multiple doses per day; the valsartan is administered in an amount of about 80 milligrams to about 320 milligrams as a single dose or as multiple doses per day.

Suitable angiotensin-converting enzyme inhibitors (ACE inhibitors) include, but are not limited to, alacepril, benazepril (LOTENSIN®, CIBACEN®), benazeprilat, captopril, ceronapril, cilazapril, delapril, duinapril, enalapril, enelaprilat, fasidotril, fosinopril, fosinoprilat, gemopatrilat, glycopril, idrapril, imidapril, lisinopril, moexipril, moveltipril, naphthopidil, omapatrilat, pentopril, perindopril, perindoprilat, quinapril, quinaprilat, ramipril, ramiprilat, rentipril, saralasin acetate, spirapril, temocapril, trandolapril, trandolaprilat, urapidil, zofenopril, acylmercapto and mercaptoalkanoyl pralines, carboxyalkyl dipeptides, carboxyalkyl dipeptide, phosphinylalkanoyl pralines, registry no. 796406, AVE 7688, BP1.137, CHF 1514, E 4030, ER 3295, FPL-66564, MDL 100240, RL 6134, RL 6207, RL 6893, SA 760, S-5590, Z 13752A, and the like. One skilled in the art will appreciate that the angiotensin-converting enzyme inhibitors may be administered in the form of pharmaceutically acceptable salts, hydrates, acids and/or stereoisomers thereof. Suitable angiotensin-converting enzyme inhibitors are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

In some embodiments the angiotensin-converting enzyme inhibitors are benazepril, captopril, enalapril, fosinopril, lisinopril, moexipril, quinapril, ramipril, trandolapril or trandolaprilat. In more particular embodiments the benazepril is administered as benazepril hydrochloride in an amount of about 5 milligrams to about 80 milligrams as a single dose or as multiple doses per day; the captopril is administered in an amount of about 12.5 milligrams to about 450 milligrams as a single dose or as multiple doses per day; the enalapril is administered as enalapril maleate in an amount of about 2.5 milligrams' to about 40 milligrams as a single dose or as multiple doses per day; the fosinopril is administered as fosinopril sodium in an amount of about 5 milligrams to about 60 milligrams as a single dose or as multiple doses per day; the lisinopril is administered in an amount of about 2.5 milligrams to about 75 milligrams as a single dose or as multiple doses per day; the moexipril is administered as moexipril hydrochloride in an amount of about 7.5 milligrams to about 45 milligrams as a single dose or as multiple doses per day; the quinapril is administered as quinapril hydrochloride in an amount of about 5 milligrams to about 40 milligrams as single or multiple doses per day; the ramipril hydrochloride is administered in an amount of about 1.25 milligrams to about 40 milligrams as single or multiple doses per day; the trandolapril is administered in an amount of about 0.5 milligrams to about 4 milligrams as single or multiple doses per day; the trandolaprilat is administered in an amount of about 0.5 milligrams to about 4 milligrams as single or multiple doses per day.

Suitable antidiabetic compounds include but are not limited to, acarbose, acetohexamide, buformin, carbutamide, chlorpropamide, glibornuride, gliclazide, glimepiride, glipizide, gliquidone, glisoxepide, glyburide, glybuthiazol(e), glybuzole, glyhexamide, glymidine, glypinamide, insulin, metformin, miglitol, nateglinide, phenbutamide, phenformin, pioglitazone, repaglinide, rosiglitazone, tolazamide, tolbutamide, tolcyclamide, troglitazone, voglibose, and the like. Suitable antidiabetic compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable anti-hyperlipidemic compounds include, but are not limited to, statins or HMG-CoA reductase inhibitors, such as, for example, atorvastatin (LIPITOR®), bervastatin, cerivastatin (BAYCOL®), dalvastatin, fluindostatin (Sandoz XU-62-320), fluvastatin, glenvastatin, lovastatin (MEVACOR®), mevastatin, pravastatin (PRAVACHOL®), rosuvastatin (CRESTRO®), simvastatin (ZOCOR®), velostatin (also known as synvinolin), VYTORIN™ (ezetimibe/simvastatin), GR-95030, SQ 33,600, BMY 22089, BMY 22,566, CI-980, and the like; gemfibrozil, cholystyramine, colestipol, niacin, nicotinic acid, bile acid sequestrants, such as, for example, cholestyramine, colesevelam, colestipol, poly(methyl-(3-trimethylaminopropyl)imino-trimethylene dihalide) and the like; probucol; fibric acid agents or fibrates, such as, for example, bezafibrate (Bezalip™), beclobrate, binifibrate, ciprofibrate, clinofibrate, clofibrate, etofibrate, fenofibrate (Lipidil™, Lipidil Micro™), gemfibrozil (Lopid™.), nicofibrate, pirifibrate, ronifibrate, simfibrate, theofibrate and the like; cholesterol ester transfer protein (CETP) inhibitors, such as for example, CGS 25159, CP-529414 (torcetrapid), JTT-705, substituted N-[3-(1,1,2,2-tetrafluoroethoxy)benzyl]-N-(3-phenoxyphenyl)-trifluoro-3-amino-2-propanols, N,N-disubstituted trifluoro-3-amino-2-propanols, PD 140195 (4-phenyl-5-tridecyl-4H-1,2,4-triazole-3-thiol), SC-794, SC-795, SCH 58149, and the like.

In some embodiments the anti-hyperlipidemic compounds are atorvastatin, fluvastatin, lovastatin, pravastatin, rosuvastatin or simvastatin. In more particular embodiments the atorvastatin is administered in an amount of about 10 milligrams to about 80 milligrams as a single dose or as multiple doses per day; the fluvastatin is administered in an amount of about 20 milligrams to about 80 milligrams as a single dose or as multiple doses per day; the lovastatin is administered in an amount of about 10 milligrams to about 80 milligrams as a single dose or as multiple doses per day; the pravastatin is administered in an amount of about 10 milligrams to about 80 milligrams as a single dose or as multiple doses per day; the rosuvastatin is administered in an amount of about 5 milligrams to about 40 milligrams as a single dose or as multiple doses per day; the simvastatin is administered in an amount of about 5 milligrams to about 80 milligrams as a single dose or as multiple doses per day.

Suitable antioxidants include, but are not limited to, small-molecule antioxidants and antioxidant enzymes. Suitable small-molecule antioxidants include, but are not limited to, hydralazine compounds, glutathione, vitamin C, vitamin E, cysteine, N-acetyl-cysteine, β-carotene, ubiquinone, ubiquinol-10, tocopherols, coenzyme Q, superoxide dismutase mimetics, such as, for example, 2,2,6,6-tetramethyl-1-piperidinyloxy (TEMPO), DOXYL, PROXYL, nitroxide compounds; 4-hydroxy-2,2,6,6-tetramethyl-1-piperidinyloxy (Tempol), M-40401, M-40403, M-40407, M-40419, M-40484, M-40587, M-40588, and the like. Suitable antioxidant enzymes include, but are not limited to, superoxide dismutase, catalase, glutathione peroxidase, NADPH oxidase inhibitors, such as, for example, apocynin, aminoguanidine, ONO 1714, S17834 (benzo(b)pyran-4-one derivative), and the like; xanthine oxidase inhibitors, such as, for example, allopurinol, oxypurinol, amflutizole, diethyldithiocarbamate, 2-styrylchromones, chrysin, luteolin, kaempferol, quercetin, myricetin, isorharnnetin, benzophenones such as 2,2',4,4'-tetrahydroxybenzophenone, 3,4,5,2',3',4'-hexahydroxybenzophenone and 4,4'-dihydroxybenzophenone; benzothiazinone analogues such as 2-amino-4H-1,3-benzothiazin-4-one, 2-guanidino-4H-1,3-benzothiazin-4-one and rhodanine; N-hydroxyguanidine derivative such as, PR5 (1-(3,4-dimethoxy-2-chlorobenzylideneamino)-3-hydroxyguanidine); 6-formylpterin, and the like. The antioxidant enzymes can be delivered by gene therapy as a viral vertor and/or a non-viral vector. Suitable antioxidants are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the antioxidants are apocynin, hydralazine compounds and superoxide dimutase mimetics.

Suitable antithrombotic and vasodilator compounds include, but are not limited to, abciximab, acetorphan, acetylsalicylic acid, argatroban, bamethan, benfurodil, benziodarone, betahistine, bisaramil, brovincamine, bufeniode, citicoline, clobenfurol, clopidogrel, cyclandelate, dalteparin, dipyridamol, droprenilamine, enoxaparin, fendiline, ifenprodil, iloprost, indobufen, isobogrel, isoxsuprine, heparin, lamifiban, midrodine, nadroparin, nicotinoyl alcohol, nylidrin, ozagrel, perhexyline, phenylpropanolamine, prenylamine, papaveroline, reviparin sodium salt, ridogrel, suloctidil, tinofedrine, tinzaparin, trifusal, vintoperol, xanthinal niacinate, and the like. Suitable antithrombotic and vasodilator compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable antithrombotic and vasodilator compounds include, but are not limited to, abciximab, acetorphan, acetylsalicylic acid, argatroban, bamethan, benfurodil, benziodarone, betahistine, bisaramil, brovincamine, bufeniode, citicoline, clobenfurol, clopidogrel, cyclandelate, dalteparin, dipyridamol, droprenilamine, enoxaparin, fendiline, ifenprodil, iloprost, indobufen, isobogrel, isoxsuprine, heparin, lamifiban, midrodine, nadroparin, nicotinoyl alcohol, nylidrin, ozagrel, perhexyline, phenylpropanolamine, prenylamine, papaveroline, reviparin sodium salt, ridogrel, suloctidil, tinofedrine, tinzaparin, trifusal, vintoperol, xanthinal niacinate, and the like. Suitable antithrombotic and vasodilator compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable β-adrenergic antagonists include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, butofilolol, carazolol, capsinolol, carteolol, carvedilol (COREG®), celiprolol, cetamolol, cindolol, cloranolol, dilevalol, diprafenone, epanolol, ersentilide, esmolol, esprolol, hydroxalol, indenolol, labetalol, landiolol, laniolol, levobunolol, mepindolol, methylpranol, metindol, metipranolol, metrizoranolol, metoprolol, moprolol, nadolol, nadoxolol, nebivolol, nifenalol, nipradilol, oxprenolol, penbutolol, pindolol, practolol, pronethalol, propranolol, sotalol, sotalolnadolol, sulfinalol, taliprolol, talinolol, tertatolol, tilisolol, timolol, toliprolol, tomalolol, trimepranol, xamoterol, xibenolol, 2-(3-(1,1-dimethylethyl)-amino-2-hydroxypoxy)-3-pyridenecarbonitrilHCl, 1-butylamino-3-(2,5- dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide, Acc 9369, AMO-140, BIB-16S, CP-331684, Fr-172516, ISV-208, L-653328, LM-2616, SB-226552, SR-58894A, SR-59230A, TZC-5665, UK-1745, YM-430, and the like. Suitable β-adrenergic antagonists are described more fully in the literature, such as in Goodman and Gilman, The Pharmacological Basis of Therapeutics (9th Edition), McGraw-Hill, 1995; and the Merck Index on CD-ROM, 13$^{th}$ Edition; and on STN Express, file phar and file registry.

In some embodiments the β-adrenergic antagonists are atenolol, bisoprolol, carvedilol, metoprolol, nebivolol, propranolol or timolol. In more particular embodiments the atenolol is administered in an amount of about 50 milligrams to about 200 milligrams as a single dose or as multiple doses per day; the bisoprolol is administered as bisoprolol fumarate in an amount of about 2.5 milligrams to about 30 milligrams as a single dose or as multiple doses per day; the carvedilol is administered in an amount of about 3.125 milligrams to about 200 milligrams as a single dose or as multiple doses per day; the metoprolol is administered as metoprolol tartarate or metoprolol succinate in an amount of about 25 milligrams to about 300 milligrams as a single dose or as multiple doses per day; the nebivolol is administered as nebivolol hydrochloride in an amount of about 2.5 milligrams to about 20 milligrams as a single dose or as multiple doses per day; the propranolol is administered as propranolol hydrochloride in an amount of about 40 milligrams to about 240 milligrams as a single dose or as multiple doses per day; the timolol is administered as timolol maleate in an amount of about 10 milligrams to about 30 milligrams as a single dose or as multiple doses per day.

Suitable calcium channel blockers include, but are not limited to, amlodipine (NORVASC®), anipamil, aranidipine, aminone, azelnidipine, barnidipine, bencyclane, benidipine, bepridil, cilnidipine, cinnarizine, clentiazem, diltiazem, dotarizine, efonidipine, elgodipine, fantofarone, felodipine, fendiline, flunarizine, fluspirilene, fumidipine, gallopamil, ipenoxazone, isradipine, lacidipine, lemildipine, lercanidipine, lomerizine, manidipine, mibefradil, monatepil, nicardipine, nifedipine, niguldipine, niludipine, nilvadipine, nimodipine, nisoldipine, nitrendipine, nivaldipine, oxodipine, perhexylene, phenyloin, phenylprenylamine, pranidipine, ranolazine, ryosidine, semotiadil, tamolarizine, temiverine hydrochloride, terodiline, tiapamil, vatanidipine hydrochloride, verapamil, ziconotide, AE-0047, CAI, JTV-519, CHF-1521, L-651582, NS-7, NW-1015, RO-2933, SB-237376, SL-34.0829-08, S-312d, SD-3212, TA-993, YM-430, and the like. Suitable calcium channel blockers are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the calcium channel blockers are amlodipine, diltiazem, isradipine, nicardipine, nifedipine, nimodipine, nisoldipine, nitrendipine, verapamil.

Suitable endothelin antagonists include, but are not limited to, atrasentan, bosentan, darusentan, endothelin, enrasentan, sitaxsentan, sulfonamide endothelin antagonists, tezosentan, BMS193884, BQ-123, SQ 28608, and the like. Suitable endothelin antagonists are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable hydralazine compounds include, but are not limited to, compounds having the formula:

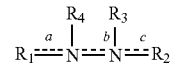

wherein a, b and c are independently a single or double bond; $R_1$ and $R_2$ are each independently a hydrogen, an alkyl, an ester or a heterocyclic ring, wherein alkyl, ester and heterocyclic rind are as defined herein; $R_3$ and $R_4$ are each independently a lone pair of electrons or a hydrogen, with the proviso that at least one of $R_1$, $R_2$, $R_3$ and $R_4$ is not a hydrogen. Exemplary hydralazine compounds include budralazine, cadralazine, dihydralazine, endralazine, hydralazine, pildralazine, todralazine, and the like. Suitable hydralazine compounds are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the hydralazine compound is hydralazine or a pharmaceutically acceptable salt thereof such as hydralazine hydrochloride. In more particular embodiments the hydralazine is administered as hydralazine hydrochloride in an amount of about 10 milligrams to about 300 milligrams as a single dose or as multiple doses per day.

Suitable $H_2$ receptor antagonists include, but are not limited to, burimamide, cimetidine, ebrotidin, famotidine, nizatidine, roxatidine, rantidine, tiotidine, and the like. Suitable $H_2$ receptor antagonists are described more fully in the literature, such as in Goodman and Gilman, The Pharmacological Basis of Therapeutics (9th Edition), McGraw-Hill, 1995, Pgs. 901-915; the Merck Index on CD-ROM, 13$^{th}$ Edition; and in WO 00/28988 assigned to NitroMed. Inc., the disclosures of which are incorporated herein by reference in their entirety.

Suitable neutral endopeptidase inhibitors include, but are not limited to, atrial natriuretic peptides, diazapins, azepinones, ecadotril, fasidotril, fasidotrilat, omapatrilat, sampatrilat, BMS 189,921, Z 13752 A, and the like. Neutral endopeptidase inhibitors are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable NSAIDs include, but are not limited to, acetaminophen, acemetacin, aceclofenac, alminoprofen, amfenac, bendazac, benoxaprofen, bromfenac, bucloxic acid, butibufen, carprofen, cinmetacin, clopirac, diclofenac, etodolac, felbinac, fenclozic acid, fenbufen, fenoprofen, fentiazac, flunoxaprofen, flurbiprofen, ibufenac, ibuprofen, indomethacin, isofezolac, isoxepac, indoprofen, ketoprofen, lonazolac, loxoprofen, metiazinic acid, mofezolac, miroprofen, naproxen, oxaprozin, pirozolac, pirprofen, pranoprofen, protizinic acid, salicylamide, sulindac, suprofen, suxibuzone, tiaprofenic acid, tolmetin, xenbucin, ximoprofen, zaltoprofen, zomepirac, aspirin, acemetcin, bumadizon, carprofenac, clidanac, diflunisal, enfenamic acid, fendosal, flufenamic acid, flunixin, gentisic acid, ketorolac, meclofenamic acid, mefenamic acid, mesalamine, prodrugs thereof, and the like. Suitable NSAIDs are described more fully in the literature, such as in Goodman and Gilman, The Pharmacological Basis of Therapeutics (9th Edition), McGraw-Hill, 1995, Pgs. 617-657; the Merck Index on CD-ROM, 13$^{th}$ Edition; and in U.S.

Pat. Nos. 6,057,347 and 6,297,260 assigned to NitroMed. Inc., the disclosures of which are incorporated herein by reference in their entirety.

In some embodiments the NSAIDs are acetaminophen, diclofenac, flurbiprofen, ibuprofen, indomethacin, ketoprofen, naproxen or aspirin. In more particular embodiments the acetaminophen is administered in an amount of about 325 milligrams to about 4 grams as a single dose or as multiple doses per day; the diclofenac is administered in an amount of about 50 milligrams to about 250 milligrams as a single dose or as multiple doses per day; the flurbiprofen is administered in an amount of about 100 milligrams to about 300 milligrams as a single dose or as multiple doses per day; the ibuprofen is administered in an amount of about 400 milligrams to about 3.2 grams as a single dose or as multiple doses per day; the indomethacin is administered in an amount of about 25 milligrams to about 200 milligrams as a single dose or as multiple doses per day; the ketoprofen is administered in an amount of about 50 milligrams to about 300 milligrams as a single dose or as multiple doses per day; the naproxen is administered in an amount of about 250 milligrams to about 1.5 grams as a single dose or as multiple doses per day; the aspirin is administered in an amount of about 10 milligrams to about 2 grams as a single dose or as multiple doses per day.

Suitable phosphodiesterase inhibitors include but are not limited to, filaminast, piclamilast, rolipram, Org 20241, MCI-154, roflumilast, toborinone, posicar, lixazinone, zaprinast, sildenafil, pyrazolopyrimidinones, motapizone, pimobendan, zardaverine, siguazodan, CI-930, EMD 53998, imazodan, saterinone, loprinone hydrochloride, 3-pyridinecarbonitrile derivatives, acefylline, albifylline, bamifylline, denbufylline, diphylline, doxofylline, etofylline, torbafylline, theophylline, nanterinone, pentoxofylline, proxyphylline, cilostazol, cilostamide, MS 857, piroximone, milrinone, aminone, tolafentrine, dipyridamole, papaveroline, E4021, thienopyrimidine derivatives, triflusal, ICOS-351, tetrahydropiperazino (1,2-b)beta-carboline-1,4-dione derivatives, carboline derivatives, 2-pyrazolin-5-one derivatives, fused pyridazine derivatives, quinazoline derivatives, anthranilic acid derivatives, imidazoquinazoline derivatives, tadalafil, vardenafil, and in Goodman and Gilman, The Pharmacological Basis of Therapeutics (9th Ed.), McGraw-Hill, Inc. (1995), The Physician's Desk Reference (49th Ed.), Medical Economics (1995), Drug Facts and Comparisons (1993 Ed), Facts and Comparisons (1993), and the Merck Index on CD-ROM, 13$^{th}$ Edition; and the like. Phosphodiesterase inhibitors and their nitrosated and/or nitrosylated derivatives are also disclosed in U.S. Pat. Nos. 5,932,538, 5,994,294, 5,874,437, 5,958,926 reissued as U.S. Pat. Nos. RE 0,377,234 6,172,060, 6,197,778, 6,177,428, 6,172,068, 6,221,881, 6,232,321, 6,197,782, 6,133,272, 6,211,179, 6,316,457 and 6,331,542, the disclosures of each of which are incorporated herein by reference in their entirety.

Suitable potassium channel blockers include but are not limited to, nicorandil, pinacidil, cromakalim (BRL 34915), aprikalim, bimakalim, emakalim, lemakalim, minoxidil, diazoxide, 9-chloro-7-(2-chlorophenyl)-5H-pyrimido(5,4,-d)(2)-benzazepine, Ribi, CPG-11952, CGS-9896, ZD 6169, diazixide, Bay X 9227, P1075, Bay X 9228, SDZ PCO 400, WAY-120,491, WAY-120,129, Ro 31-6930, SR 44869, BRL 38226, S 0121, SR 46142A, CGP 42500, SR 44994, artilide fumarate, lorazepam, temazepam, rilmazafone, nimetazepam, midazolam, lormetazepam, loprazolam, ibutilide fumarate, haloxazolam, flunitrazepam, estazolam, doxefazepam, clonazepam, cinolazepam, brotizolam, and the like. Suitable potassium channel blockers are described more fully in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable platelet reducing agents include but are not limited to, fibrinolytic agents such as for example, ancrod, anistreplase, bisobrin lactate, brinolase, Hageman factor (i.e. factor XII) fragments, plasminogen activators such as, for example, streptokinase, tissue plasminogen activators (TPA), urokinase, pro-Urokinase, recombinant TPA, plasmin, plasminogen, and the like; anti-coagulant agents including but are not limited to, inhibitors of factor Xa, factor TFPI, factor VIIa, factor IXc, factor Va, factor VIIIa, inhibitors of other coagulation factors, and the like; vitamin K antagonists, such as, for example, coumarin, coumarin derivatives (e.g., warfarin sodium); glycosoaminoglycans such as, for example, heparins both in unfractionated form and in low molecular weight form; ardeparin sodium, bivalirudin, bromindione, coumarin, dalteparin sodium, danaparoid sodium; dazoxiben hydrochloride, desirudin, dicumarol, efegatran sulfate, enoxaparin sodium, ifetroban, ifetroban sodium, lyapolate sodium, nafamostat mesylate, phenprocoumon, sulfatide, tinzaparin sodium, retaplase; trifenagrel, warfarin, dextrans and the like; abciximab, acadesine, anipamil, argatroban, aspirin, clopidogrel, diadenosine 5',5'''-P1,P4-tetraphosphate (Ap4A) analogs, difibrotide, dilazep dihydrochloride, dipyridamole, dopamine, 3-methoxytyramine, glucagon, glycoprotein IIb/IIIa antagonists, such as, for example, Ro-43-8857, L-700,462, iloprost, isocarbacyclin methyl ester, itazigrel, ketanserin, BM-13.177, lamifiban, lifarizine, molsidomine, nifedipine, oxagrelate, prostaglandins, platelet activating factor antagonists such as, for example, lexipafant, prostacyclins, pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612, ZK-36374, 2,4,5,7-tetrathiaoctane, 2,4,5,7-tetrathiaoctane 2,2-dioxide, 2,4,5-trithiahexane, theophylline pentoxifylline, thromboxane and thromboxane synthetase inhibitors such as, for example, picotamide, sulotroban, ticlopidine, tirofiban, trapidil, ticlopidine, trifenagrel, trilinolein, 3-substituted 5,6-bis(4-methoxyphenyl)-1,2,4-triazines; antibodies to glycoprotein IIb/Iha; antiserotonin drugs, such as, for example, clopridogrel; sulfinpyrazone and the like; aspirin; dipyridamole; clofibrate; pyridinol carbamate; glucagon, caffeine; theophyllin pentoxifyllin; ticlopidine, and the like.

Suitable proton pump inhibitors include, but are not limited to, disulprazole, esomeprazole, lansoprazole, leminoprazole, omeprazole, pantoprazole, rabeprazole, timoprazole, tenatoprazole, 2-(2-benzimidazolyl)-pyridine, tricyclic imidazole, thienopydidine benzimidazole, fluoroalkoxy substituted benzimidazole, dialkoxy benzimidazole, N-substituted 2-(pyridylalkenesulfinyl)benzimidazole, cycloheptenepyridine, 5-pyrrolyl-2-pyridylmethylsulfinyl benzimidazole, alkylsulfinyl benzimidazole, fluoro-pyridylmethylsulfinyl benzimidazole, imidazo(4,5-b)pyridine, RO 18-5362, IY 81149, 4-amino-3-carbonyl quinoline, 4-amino-3-acylnaphthyride, 4-aminoquinoline, 4-amino-3-acylquinoline, 3-butyryl-4-(2-methylphenylamino)-8-(2-hydroxyethoxy)quinoline, quinazoline, tetrahydroisoquinolin-2-yl pyrimidine, YH 1885, 3-substituted 1,2,4-thiadiazolo(4,5-a) benzimidazole, 3-substituted imidazo(1,2-d)-thiadiazole, 2-sulfinylnicotinamide, pyridylsulfinylbenz imidazole, pyridylsulfinyl thieno imidazole, theinoimidazole-toluidine, 4,5-dihydrooxazole, thienoimidazole-toluidine, Hoe-731, imidazo(1,2-a)pyridine, pyrrolo(2,3-b)pyridine, and the like. Suitable proton pump inhibitors are described more fully in the literature, such as in Goodman and Gilman, The Pharmacological Basis of Therapeutics (9th Edition), McGraw-Hill, 1995; the Merck Index on CD-ROM, 13$^{th}$ Edition; and in WO 00/50037 assigned to NitroMed Inc., the disclosures of which are incorporated herein by reference in their entirety.

Suitable renin inhibitors include, but are not limited to, aldosterone, aliskiren (SPP-100), ditekiren, enalkrein (A-64662), medullipin, terlkiren, tonin, zankiren, RO 42-5892 (remikiren), A 62198, A 64662, A 65317, A 69729, A 72517 (zankiren), A 74273, CP 80794, CGP 29287, CGP-38560A, EMD 47942, ES 305, ES 1005, ES 8891, FK 906, FK 744, H 113, H-142, KRI 1314, pepstatin A, RO 44-9375 (ciprokiren), RO 42-5892, RO 66-1132, RO 66-1168, SP 500, SP 800, SR-43845, SQ 34017, U 71038, YM-21095, YM-26365, urea derivatives of peptides, amino acids connected by nonpeptide bonds, di- and tri-peptide derivatives (e.g., Act-A, Act-B, Act-C, ACT-D, and the like), amino acids and derivatives thereof, diol sulfonamides and sulfinyls, modified peptides, peptidyl beta-aminoacyl aminodiol carbamates, monoclonal antibodies to renin. Suitable renin inhibitors are described more fully in U.S. Pat. Nos. 5,116,835, 5,114,937, 5,106,835, 5,104,869, 5,095,119, 5,098,924), 5,095,006, 5,089,471, 5,075,451, 5,066,643, 5,063,208, 4,845,079, 5,055,466, 4,980,283, 4,885,292), 4,780,401, 5,071,837, 5,064,965, 5,063,207, 5,036,054, 5,036,053, 5,034,512, and 4,894,437, the disclosures of each of which are incorporated herein by reference in their entirety; and in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

Suitable COX-2 inhibitors include, but are not limited to, nimesulide, celecoxib (CELEBREX®), etoricoxib (ARCOXIA®), flosulide, lumiracoxib (PREXIG®, COX-189), parecoxib (DYNSTAT®), rofecoxib (VIOXX®), tiracoxib (JTE-522), valdecoxib (BEXTRA®), ABT 963, BMS 347070, CS 502, DuP 697, GW-406381, NS-386, SC-57666, SC-58125, SC-58635, and the like, and mixtures of two or more thereof. Suitable COX-2 inhibitors are in U.S. Pat. Nos. 5,344,991, 5,380,738, 5,393,790, 5,409,944, 5,434,178, 5,436,265, 5,466,823, 5,474,995, 5,510,368, 5,536,752, 5,550,142, 5,552,422, 5,604,253, 5,604,260, 5,639,780, 5,932,598 and 6,633,272, and in WO 94/03387, WO 94/15723, WO 94/20480, WO 94/26731, WO 94/27980, WO 95/00501, WO 95/15316, WO 96/03387, WO 96/03388, WO 96/06840, WO 96/21667, WO 96/31509, WO 96/36623, WO 97/14691, WO 97/16435, WO 01/45703 and WO 01/87343, the disclosures of each of which are incorporated herein by reference in their entirety; and in the literature, such as in Goodman and Gilman, The Pharmacological Basis of Therapeutics (9th Edition), McGraw-Hill, 1995; and the Merck Index on CD-ROM, Thirteenth Edition; and on STN Express, file phar and file registry.

In some embodiments the COX-2 inhibitors are celecoxib, etoracoxib, lumiracoxib, paracoxib, rofecoxib or valdecoxib. In more particular embodiments the celecoxib is administered in an amount of about 100 milligrams to about 800 milligrams as a single dose or as multiple doses per day; the etoricoxib is administered in an amount of about 50 milligrams to about 200 milligrams as a single dose or as multiple doses per day; the lumiracoxib is administered in an amount of about 40 milligrams to about 1200 milligrams as a single dose or as multiple doses per day; the paracoxib is administered in an amount of about 20 milligrams to about 100 milligrams as a single dose or as multiple doses per day; the rofecoxib is administered in an amount of about 12.5 milligrams to about 50 milligrams as a single dose or as multiple doses per day; the valdecoxib is administered in an amount of about 10 milligrams to about 40 milligrams as a single dose or as multiple doses per day.

The invention provides compositions comprising (i) a furoxan compound comprising at least two furoxan moieties, (ii) a nitric oxide enhancing compound, such as, isosorbide dinitrate and/or isosorbide mononitrate (preferably isosorbide dinitrate), and (iii) a hydralazine compound (such as hydralazine hydrochloride). In one embodiment, the hydralazine hydrochloride can be administered in an amount of about 30 milligrams per day to about 400 milligrams per day; the isosorbide dinitrate can be administered in an amount of about 10 milligrams per day to about 200 milligrams per day; or the isosorbide mononitrate can be administered in an amount of about 5 milligrams per day to about 120 milligrams per day. In another embodiment, the hydralazine hydrochloride can be administered in an amount of about 50 milligrams per day to about 300 milligrams per day; the isosorbide dinitrate can be administered in an amount of about 20 milligrams per day to about 160 milligrams per day; or the isosorbide mononitrate can be administered in an amount of about 15 milligrams per day to about 100 milligrams per day. In yet another embodiment, the hydralazine hydrochloride can be administered in an amount of about 37.5 milligrams to about 75 milligrams one to four times per day; the isosorbide dinitrate can be administered in an amount of about 20 milligrams to about 40 milligrams one to four times per day; or the isosorbide mononitrate can be administered in an amount of about 10 milligrams to about 20 milligrams one to four times per day. In another embodiment of the methods of the invention, the patient can be administered a composition comprising about 225 mg hydralazine hydrochloride and about 120 mg isosorbide dinitrate once per day (i.e., q.d.). In another embodiment of the methods of the invention, the patient can be administered a composition comprising about 112.5 mg hydralazine hydrochloride and about 60 mg isosorbide dinitrate twice per day (i.e., b.i.d.). In another embodiment of the methods of the invention, the patient can be administered a composition comprising about 56.25 mg hydralazine hydrochloride and about 30 mg isosorbide dinitrate twice per day (i.e., b.i.d.). In another embodiment of the methods of the invention, the patient can be administered a composition comprising about 75 mg hydralazine hydrochloride and about 40 mg isosorbide dinitrate three times per day (i.e., t.i.d.). In another embodiment of the methods of the invention, the patient can be administered a composition comprising about 37.5 mg hydralazine hydrochloride and about 20 mg isosorbide dinitrate three times per day (i.e., t.i.d.). The particular amounts of hydralazine and isosorbide dinitrate or isosorbide mononitrate can be administered as a single dose once a day; or in multiple doses several times throughout the day; or as a sustained-release oral formulation, or as an injectable formulation.

The furoxan compound, and, optionally, nitric oxide enhancing compounds and/or therapeutic agent, can be incorporated into a natural or synthetic matrix which can then be applied with specificity to a biological site of interest. Accordingly the furoxan compound, and, optionally, nitric oxide enhancing compound and/or therapeutic agent is "bound to the matrix" which means that the furoxan compound, and, optionally, nitric oxide enhancing compound and/or therapeutic agent, are physically and/or chemically associated with part of, incorporated with, attached to, or contained within the natural or synthetic matrix. In one embodiment, physical association or bonding can be achieved, for example, by coprecipitation of the furoxan compound, and, optionally, nitric oxide enhancing compound and/or therapeutic agent, with the matrix. In another embodiment, chemical association or bonding can be achieved by, for example, covalent bonding of a nucleophilic moiety of the furoxan compound of the invention and optionally nitric oxide enhancing compound, and/or therapeutic agent, to the matrix, such that the furoxan compound, is part of the matrix itself. In yet another embodiment, the furoxan compound, and, optionally, nitric oxide enhancing compound, and/or therapeutic agent can be incorporated into a porous layer of the matrix or into pores included in the natural or synthetic matrix. The manner in which the furoxan compound, and, optionally, nitric oxide enhancing compound and/or therapeutic agent, is associated, part of, attached to, incorporated with or contained within (i.e. "bound to") the matrix is inconsequential to the invention and all means of association, incorporation, attachment, and bonding are contemplated herein. Incorporation of the furoxan compounds and optionally nitric oxide enhancing compounds and/or therapeutic agents, into the matrix results in site-specific application, thereby enhancing selectivity of action for the released nitric oxide and the furoxan compound. Additionally, incorporation of the furoxan compound into the matrix reduces the rate of release of the nitric oxide and the furoxan compound. This prolongs the release of the nitric oxide and the furoxan compound thereby allowing for efficient dosing to achieve a desired biological effect so that the frequency of dosing can be reduced.

Any of a wide variety of natural or synthetic polymers can be used as the matrix in the context of the invention. It is only necessary for the matrix to be biologically acceptable. Exemplary matrixes suitable for use in the invention are polymers including, for example, polyolefins (such as, polystyrene, polyalkylenes, polypropylene, polyethylene, high molecular weight polyethylene, polyethylene oxides, high density polyethylene, polytetrafluorethylene, polyvinylidene difluoride and polyvinylchloride), polyethylenimine or derivatives thereof, polyethers (such as, polyethylene glycol), polyesters (such as, poly-L-lactic acid, poly-D, L-lactic, poly-D-lactic, polyglycolic acid, poly-(lactide/glycolide, polyethylene terephthalate), polyether sulfones, polyanhydrides, polyhydroxybutyrates, polyamides (such as, nylon), polyurethanes, polyurethane copolymers (such as, pellethane polymers), polyacrylates (such as, polymethacrylate, poly (2-(methacryloyloxyethyl)-2'-(trimethylammonium)ethyl phosphate inner salt-co-n-dodecyl methacrylate, methylmethacrylate), polyvinylpyrrolidones, cross-linked polyvinylpyrrolidones, polyvinyl alcohols, polyvinyl acetates, halogenated polyalkylenes, polyvinyl ethers, polyvinyl aromatics, polyurethanes, polyorthoesters, polycarbonates, polyalkylenes, polycarboxylic acids (such as, for example polyacrylic acids), polycaprolactone, polyhydroxybutyrate valerate, silicones, siloxane polymers, hyaluronic acid, mixtures of polymers (such as, polylactic acid/polylysine copolymers, polyalkylene/styrene copolymers, polyurethane/polyester copolymers, polyurethane/polyether copolymers, polyethylene oxide/polypropylene oxides, ethylene-vinyl acetate copolymers, nylon/polyether copolymers, such as vestamid), biopolymers (such as peptides, polypeptides, proteins, chitosan, chitosan derivatives, gelatin, oligonucleotides, antibodies, peptide hormones, glycoproteins, glycogen and nucleic acids, fibrin, collagen), glycosaminoglycans, polysaccharides (such as, for example, cellulose, starches, dextrans, alginates, derivatives such as, cellulose acetate, cellulose nitrate), starburst dendrimers, natural fibrous matrix (such as, filter paper), synthetic fibrous matrix materials (such as, three-dimensional lattice of synthetic polymers and copolymers) and the like. Exemplary polymers are described in U.S. Pat. Nos. 5,705,583, 5,770,645, 5,994,444, 6,087,479 and 6,153,252, the disclosures of each of which are incorporated by reference herein in their entirety. In some embodiments the matrix materials are polylactic acid, polyurethane and polyalkene polymers. In another embodiment the matrix material is nitrosated and/or nitrosylated and/or contains a nitroxide moiety.

The physical and structural characteristics of the matrixes suitable for use in the invention are not critical, but depend on the application. It will be appreciated by one skilled in the art that where the matrix-compound and/or composition of the invention is intended for local, relatively short term administration or similar administration they need not be biodegradable. For some uses, such as postangioplasty, coronary bypass surgery or intimal hyperplasia associated with vascular or non-vascular graft implants or the like, it may be desirable for the matrix to slowly dissolve in a physiological environment or to be biodegradable.

The furoxan compound and, optionally, the nitric oxide enhancing compound and/or therapeutic agent bound to the matrix may be administered in a wide variety of forms or delivery means. Any delivery means should adequately protect the integrity of the nitric oxide prior to its release and should control the release of the nitric oxide at such a rate, in such an amount, and in such a location as to serve as an effective means for prevention and/or treatment of cardiovascular diseases and disorders, including restenosis. Delivery means for local administration include, but are not limited to, those described herein. Delivery means for systemic administration include, for example, solutions, suspensions, emulsions, capsules, powders, sachets, tablets, effervescent tablets, topical patches, lozenges, aerosols, liposomes, microparticles, microspheres, beads and the like. The matrix itself may be structurally sufficient to serve as a delivery means.

The furoxan compound, and, optionally, nitric oxide enhancing compound and/or therapeutic agent, bound to the matrix can also be used to coat all or a portion of the surface of a medical device that comes into contact with blood (including blood components and blood products), vascular or non-vascular tissue thereby rendering the surface passive. Alternatively the furoxan compound and the nitric oxide enhancing compound, and, optionally, the therapeutic agent, bound to the matrix can also be used to coat all or a portion of the surface of a medical device that comes into contact with blood (including blood components and blood products), vascular or non-vascular tissue thereby rendering the surface passive. U.S. Pat. Nos. 5,665,077, 5,797,887, 5,824,049 and 5,837,008, the disclosures of each of which are incorporated by reference herein in their entirety, describe methods for coating all or a portion of a surface of a medical device. Thus, for example, (i) all or a portion of the medical device may be coated with the furoxan compound, and, optionally, nitric oxide enhancing compounds and/or therapeutic agents, either as the coating per se or bound to a matrix, as described herein; or (ii) all or a portion of the medical device may be produced from a material which includes the fliroxan compound of the invention and optionally nitric oxide enhancing compound and/or therapeutic agent, per se or bound to a matrix, as described herein.

It is also contemplated that artificial surfaces will vary depending on the nature of the surface, and such characteristics including contour, crystallinity, hydrophobicity, hydrophilicity, capacity for hydrogen bonding, and flexibility of the molecular backbone and polymers. Therefore, using routine methods, one of ordinary skill will be able to customize the coating technique by adjusting such parameters as the amount of adduct, length of treatment, temperature, diluents, and storage conditions, in order to provide optimal coating of each particular type of surface.

After the medical device or artificial material has been coated with the furoxan compound, and, optionally, nitric oxide enhancing compound and/or therapeutic agent, or with the furoxan compound, and, optionally, the therapeutic agent, it will be suitable for its intended use, including, for example, implantation as a heart valve, insertion as a catheter, insertion as a stent, or for cardiopulmonary oxygenation or hemodialysis.

In another embodiment, the furoxan compound, and, optionally, nitric oxide enhancing compound and/or therapeutic agent can be directly incorporated into the pores or reservoirs of the medical device (i.e. without a matrix or polymer). A coating of a biocompatible polymer/material could be applied over the medical device which would control the diffusion of the furoxan compound, and, optionally, nitric oxide enhancing compound, and/or therapeutic agent from the pores or reservoirs of the medical device. The manner in which the compound of the furoxan invention and optionally nitric oxide enhancing compound and/or therapeutic agent, is associated, part of, attached to, incorporated with or contained within (i.e. "bound to") the medical device is inconsequential to the invention and all means of association, incorporation, attachment, and bonding are contemplated herein. Incorporation of the furoxan compound, and, optionally, nitric oxide enhancing compounds and/or therapeutic agents, into the pores or reservoirs of the medical device results in site-specific application, thereby enhancing selectivity of action for the released nitric oxide and compound of the invention. Additionally, incorporation of the furoxan compound into the pores or reservoirs of the medical device reduces the rate of release of the nitric oxide and the furoxan compound. This prolongs the release of the nitric oxide and the furoxan compound thereby allowing for efficient dosing to achieve a desired biological effect so that the frequency of dosing can be reduced.

The invention provides methods for treating cardiovascular disorders by administering to the patient in need thereof an effective amount of the compounds and/or compositions described herein. For example, the patient can be administered an effective amount of at least one furoxan compound. In another embodiment, the patient can be administered an effective amount of at least one furoxan compound, and at least one nitric oxide enhancing compound. In yet another embodiment, the patient can be administered an effective amount of at least one furoxan compound, and, at least one therapeutic agent, including but not limited to, such as, for example, thrombolytic agents, antimicrobial compounds, antiproliferative agents, antisecretory agents, anti-cancer chemotherapeutic agents, steroids, immunosuppressive agents, radiotherapeutic agents, heavy metals functioning as a radiopaque agent, biologic agents, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In another embodiment, the patient can be administered an effective amount of at least one furoxan compound, and, at least one therapeutic agent, and, at least one nitric oxide enhancing compound. In one embodiment the cardiovascular disorder is restenosis, atherosclerosis, a vascular or non-vascular complication associated with the use of a medical device, a wound associated with the use of a medical device, vascular or non-vascular wall damage, hypertension, heart failure, arterial stiffness, postmyocardial infarction, stroke and/or diastolic dysfunction. The furoxan compounds, nitric oxide enhancing compounds, and/or therapeutic agents can be administered separately or as components of the same composition in one or more pharmaceutically acceptable carriers.

The invention provides methods for inhibiting platelet aggregation and platelet adhesion caused by the exposure of blood to a medical device; treating pathological condition resulting from abnormal cell proliferation; treating transplantation rejections, treating inflammatory disease; reducing scar tissue or for inhibiting wound contraction; treating diseases resulting from oxidative stress; treating endothelial dysfunctions; and treating diseases caused by endothelial dysfunctions by administering to the patient in need thereof an effective amount of the compounds and/or compositions described herein. For example, the patient can be administered an effective amount of at least one furoxan compound. In another embodiment, the patient can be administered an effective amount of at least one furoxan compound, and at least one nitric oxide enhancing compound. In yet another embodiment, the patient can be administered an effective amount of at least one furoxan compound, and, at least one therapeutic agent, including but not limited to, such as, for example, thrombolytic agents, antimicrobial compounds, antiproliferative agents, antisecretory agents, anti-cancer chemotherapeutic agents, steroids, immunosuppressive agents, radiotherapeutic agents, heavy metals functioning as a radiopaque agent, biologic agents, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof. In another embodiment, the patient can be administered an effective amount of at least one furoxan compound, and, at least one therapeutic agent, and, at least one nitric oxide enhancing compound. In one embodiment the pathological condition resulting from abnormal cell proliferation is cancer. The furoxan compounds, nitric oxide enhancing compounds, and/or therapeutic agents can be administered separately or as components of the same composition in one or more pharmaceutically acceptable carriers.

When administered separately, the furoxan compound, nitric oxide enhancing compound and/or therapeutic agent can be administered about the same time as part of the overall treatment regimen, i.e., as a combination therapy. "About the same time" includes administering the furoxan compound, simultaneously, sequentially, at the same time, at different times on the same day, or on different days, as long as they are administered as part of an overall treatment regimen, i.e., combination therapy or a therapeutic cocktail.

When administered in vivo, the compounds and compositions of the invention can be administered in combination with pharmaceutically acceptable carriers and in dosages described herein. When the compounds and compositions of the invention are administered as a combination of at least one furoxan compound and/or at least one nitric oxide enhancing compound and/or at least one therapeutic agent, they can also be used in combination with one or more additional compounds which are known to be effective against the specific disease state targeted for treatment. The nitric oxide enhancing compounds, therapeutic agents and/or other additional compounds can be administered simultaneously with, subsequently to, or prior to administration of the furoxan compound.

The compounds and compositions of the invention can be administered by any available and effective delivery system including, but not limited to, systemically, orally, bucally, parenterally, by inhalation, by topical application, by injection, or transdermally, in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques. In one embodiment of the invention the furxoan compound is administered systemically, orally, parentally or by inhalation. Delivery means for systemic administration include, for example, solutions, suspensions, emulsions, capsules, powders, sachets, tablets, effervescent tablets, topical patches, lozenges, aerosols, liposomes, microparticles, microspheres, beads and the like.

Transdermal compound administration, which is known to one skilled in the art, involves the delivery of pharmaceutical compounds via percutaneous passage of the compound into the systemic circulation of the patient. Topical administration can also involve the use of transdermal administration such as transdemmal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

The compositions can also be applied topically using a transdermal system, such as one of an acrylic-based polymer adhesive with a resinous crosslinking agent impregnated with the composition and laminated to an impermeable backing. In a particular embodiment, the compositions of the invention are administered as a transdermal patch, more particularly as a sustained-release transdermal patch. The transdermal patches of the invention can include any conventional form such as, for example, adhesive matrix, polymeric matrix, reservoir patch, matrix or monolithic-type laminated structure, and are generally comprised of one or more backing layers, adhesives, penetration enhancers, an optionally rate controlling membrane and a release liner which is removed to expose the adhesives prior to application. Polymeric matrix patches also comprise a polymeric-matrix forming material. Suitable transdermal patches are described in more detail in, for example, U.S. Pat. Nos. 5,262,165, 5,948,433, 6,010,715 and 6,071,531, the disclosure of each of which are incorporated herein in their entirety.

Solid dosage forms for oral administration can include capsules, sustained-release capsules, tablets, sustained release tablets, chewable tablets, sublingual tablets, effervescent tablets, pills, powders, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailability of the compositions can be enhanced by micronization of the formulations using conventional techniques such as grinding, milling, spray drying and the like in the presence of suitable excipients or agents such as phospholipids or surfactants.

Sustained release dosage forms of the invention may comprise microparticles and/or nanoparticles having a therapeutic agent dispersed therein or may comprise the therapeutic agent in pure, preferably crystalline, solid form. For sustained release administration, microparticle dosage forms comprising pure, preferably crystalline, therapeutic agents are administered. The therapeutic dosage forms of this aspect of the invention may be of any configuration suitable for sustained release.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or 10 to 21 days) in prelysosomic vesicles and lysosomes. Larger microparticle therapeutic dosage forms of the invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to deliver anti-proliferative therapeutic agents.

Particular sustained release dosage forms of the invention comprise biodegradable microparticles or nanoparticles. More particularly, biodegradable microparticles or nanoparticles are formed of a polymer containing matrix that biodegrades by random, nonenzymatic, hydrolytic scissioning to release therapeutic agent, thereby forming pores within the particulate structure.

In a particular embodiment, the compositions of the invention are orally administered as a sustained release tablet or a sustained release capsule. For example, the sustained release formulations can comprise an effective amount of at least one furoxan compound or a pharmaceutically acceptable salt thereof, and, optionally at least one nitric oxide enhancing compound, or the sustained release formulations can comprise an effective amount of at least one furoxan compound or a pharmaceutically acceptable salt thereof, and at least one nitric oxide enhancing compound, and, optionally at least one therapeutic agent The compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound. In one embodiment, the pharmaceutically acceptable salts of the compounds of the invention do not include the nitrate salt.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given furoxan compound of the invention that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The invention also provides pharmaceutical kits comprising one or more containers filled with one or more of the ingredients of the pharmaceutical compounds and/or compositions of the invention, including, at least, one or more of the novel furoxan compounds, and one or more of the nitric oxide enhancing compounds described herein. Associated with such kits can be additional therapeutic agents or compositions (e.g., thrombolytic agents, antimicrobial compounds, antiproliferative agents, antisecretory agents, anti-cancer chemotherapeutic agents, steroids, immunosuppressive agents, radiotherapeutic agents, heavy metals functioning as a radiopaque agent, biologic agents, aldosterone antagonists, alpha-adrenergic receptor antagonists, angiotensin II antagonists, angiotensin-converting enzyme (ACE) inhibitors, antidiabetic compounds, anti-hyperlipidemic compounds, antioxidants, antithrombotic and vasodilator compounds, β-adrenergic antagonists, calcium channel blockers, endothelin antagonists, hydralazine compounds, $H_2$ receptor antagonists, neutral endopeptidase inhibitors, nonsteroidal antiinflammatory compounds (NSAIDs), phosphodiesterase inhibitors, potassium channel blockers, platelet reducing agents, proton pump inhibitors, renin inhibitors, selective cyclooxygenase-2 (COX-2) inhibitors, and combinations of two or more thereof), devices for administering the compositions, and notices in the form prescribed by a governmental agency regulating the manufacture, use or sale of pharmaceuticals or biological products which reflects approval by the agency of manufacture, use or sale for humans.

EXAMPLES

Example 1

Ethanamine, 2-[[5-oxido-4-(phenylsulfonyl)-1,2,5-oxadiazol-3-yl]oxy]-N,N-bis[2-[[5-oxido-4-(phenylsulfonyl)-1,2,5-oxadiazol-3-yl]oxy]ethyl]-, 2-hydroxy-1,2,3-propanetricarboxylate

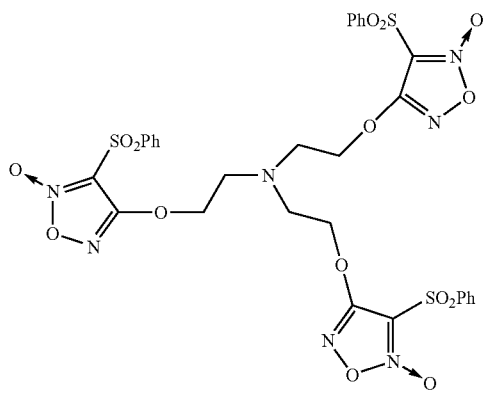

1a. Acetic acid, (phenylsulfonyl)-

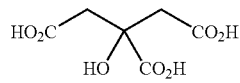

To a solution of (phenylthio)acetic acid (Aldrich, 1 g, 6 mmol) in MeOH (40 mL) was added dropwise Oxone (7.37 g, 12 mmol) in water (10 mL) at room temperature. The resultant suspension was stirred at room temperature for 2 hours. After evaporation of the solvent, the residue was triturated with cold water (15 mL), the solid was filtered, washed with water, hexane and dried under vacuum for 3 days to give the title compound (1.1 g, 92% yield) as a white solid. $^1$H NMR (400 MHz, $d_6$-DMSO) δ 7.95-7.99 (m, 2H), 7.71-7.75 (m, 1H), 7.60-7.65 (m, 2H), 4.36 (s, 2H).

1b. 1,2,5-Oxadiazole, 3,4-bis(phenylsulfonyl)-, 2-oxide

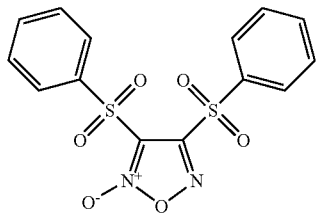

This compound was synthesized from the product of Example 1a as described by Farrer, W. V.; *J. Chem. Soc.*, 904-906 (1964). Fuming nitric acid (18 mL, 27 g, 430 mmol) was added dropwise to a suspension of the product of Example 1a (12 g, 60 mmol) in glacial acetic acid (35 mL) at 0° C. The resultant clear solution was stirred at 0° C. for 5 minutes and refluxed at 110-140° C. for 45 minutes. The reaction mixture was then cooled to room temperature and water was added. The precipitate was filtered and washed with water. The solid was recrystallized from EtOAc/$CH_2Cl_2$/Hexane to give the title compound (5.5 g, 50% yield) as a white solid. Mp 121-123° C. $^1$H NMR (400 MHz, $CDCl_3$) δ 8.15-8.20 (m, 4H), 7.78-7.84 (m, 2H), 7.60-7.70 (m, 4H). $^{13}$C NMR (100 MHz, $CDCl_3$) δ 155.7, 136.4, 137.3, 136.3, 136.0, 130.3, 130.0, 129.7, 129.3, 115.3. Mass spectrum (API-TIS) m/z 384 ($MNH_4^+$).

1c. Ethanamine, 2-[[5-oxido-4-(phenylsulfonyl)-1,2,5-oxadiazol-3-yl]oxy]-N,N-bis[2-[[5-oxido-4-(phenylsulfonyl)-1,2,5-oxadiazol-3-yl]oxy]ethyl]

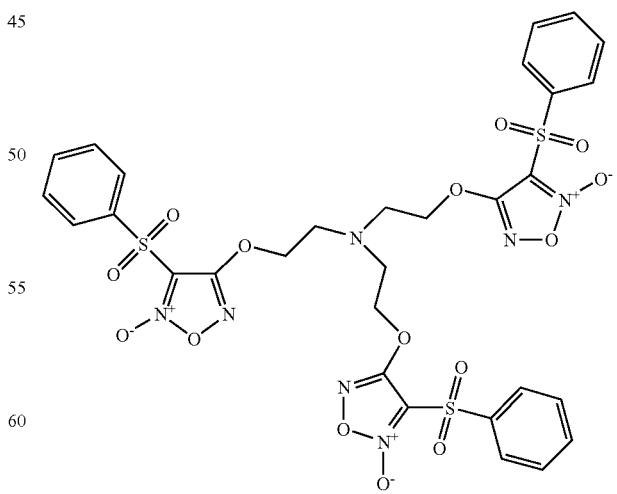

To a mixture of the product of Example 1b (5.1 g, 13.9 mmol) and triethanolamine (Aldrich, 0.54 mL, 0.61 g, 4.1 mmol) in THF (50 mL) at 0° C. under nitrogen was added dropwise an aqueous solution of NaOH (50% w/v, 2.7 g, 67.5 mmol). The resultant pale-yellow solution was stirred at 0° C. for an additional 3 hours. The reaction mixture was then diluted with ice cold EtOAc, and the solid was removed by filtration. The residue, after evaporation of the solvent, was re-dissolved in EtOAc, washed with water and dried over anhydrous $Na_2SO_4$. The solvent was evaporated. The crude material was chromatographed on silica gel eluting with (1:1:1) EtOAc:Hex:$CH_2Cl_2$ to give the title compound (1 g, 26% yield) as a white solid. Mp 113-115° C. $^1$H NMR (400 MHz, $CDCl_3$) δ 8.02-8.05 (m, 6H), 7.70-7.75 (m, 3H), 7.55-7.62 (m, 6H), 4.61 (t, J=5.2 Hz, 6H), 3.37 (t, J=5.2 Hz, 6H). $^{13}$C NMR (100 MHz, $CDCl_3$) δ 159.2, 137.9, 135.8, 129.8, 128.8, 110.8, 71.5, 54.3. Mass spectrum (API-TIS) nm/z 822 ($MH^+$). Anal. calcd for $C_{30}H_{27}N_7O_{15}S_3$: C, 43.84; H, 3.31; N, 11.98. Found: C, 44.07; H, 3.19; N, 11.74.

1d. Ethanamine, 2-[[5-oxido-4-(phenylsulfonyl)-1,2,5-oxadiazol-3-yl]oxy]-N,N-bis[2-[[5-oxido-4-(phenylsulfonyl)-1,2,5-oxadiazol-3-yl]oxy]ethyl]-, 2-hydroxy-1,2,3-propanetricarboxylate

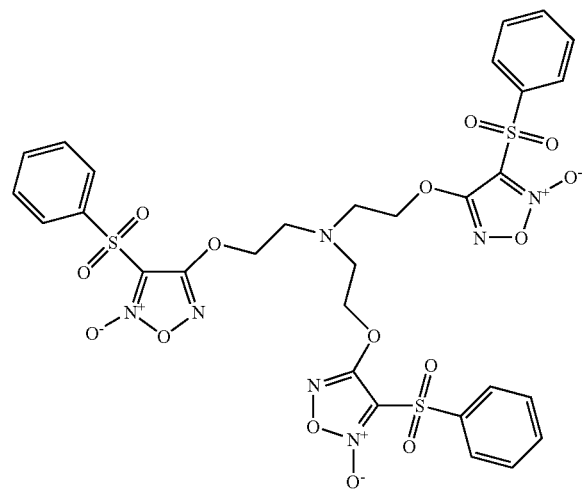

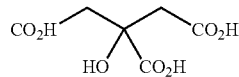

Citric acid (46.7 mg, 0.24 mmol) in MeOH (2.5 mL) was added to a solution of the product of Example 1c (0.2 g, 0.24 mmol) in EtOAc (20 mL). The reaction mixture was stirred at room temperature for 45 minutes. The solvent was evaporated, the solid filtered and washed with ice cold EtOAc and hexane to give the title compound (0.2 g, 81% yield) as a white solid. Mp 112-114° C. $^1$H NMR (400 MHz, DMSO) δ 12.10-12.40 (br s, 2H), 7.94-7.98 (m, 6H), 7.80-7.85 (m, 3H), 7.64-7.70 (m, 6H), 4.51 (br t, J=4.8 Hz, 6H), 3.19 (br t, J=4.8 Hz, 6H), 2.69 (ABq, $J_{AB}$=15.6 Hz, $\Delta v_{AB}$=41.2 Hz, 4H). Mass spectrum (API-TIS) m/z 822 ($MH^+$ for free base), 190 (M-H for citrate). Anal. calcd for $C_{36}H_{35}N_7O_{22}S_3$: C, 42.64; H, 3.48; N, 9.67. Found: C, 42.36; H, 3.23; N, 9.68.

Example 2

Ethanamine, 2-[[5-oxido-4-(phenylsulfonyl)-1,2,5-oxadiazol-3-yl]oxy]-N-[2-[[5-oxido-4-(phenylsulfonyl)-1,2,5-oxadiazol-3-yl]oxy]ethyl]-, 2-hydroxy-1,2,3-propanetricarboxylate (1:1) (salt)

2a. Ethanamine, 2-[[5-oxido-4-(phenylsulfonyl)-1,2,5-oxadiazol-3-yl]oxy]-N-[2-[[5-oxido-4-(phenylsulfonyl)-1,2,5-oxadiazol-3-yl]oxy]ethyl]

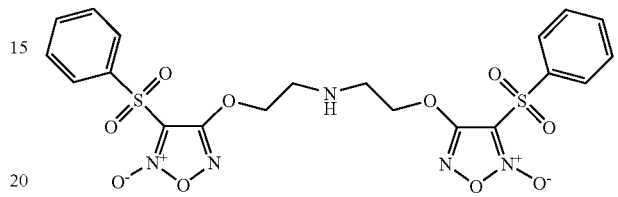

To a mixture of the product of Example 1b (2 g, 5.5 mmol) and diethanolamine (Aldrich, 0.26 mL, 0.28 g, 2.7 mmol) in THF (20 mL) at 0° C. under nitrogen was added dropwise an aqueous solution of NaOH (50% w/v, 0.87 g, 21.7 mmol) over a period of 45 minutes. The resultant pale-yellow solution was further stirred for 1 hour at 0° C. The reaction mixture was then diluted with ice cold THF (50 mL), and the solid was removed by filtration. The residue after evaporation of the solvent, was chromatographed on silica gel eluting with (1:99 to 5:95) MeOH:EtOAc to give the title compound (0.55 g, 36% yield) as a white solid. Mp 116-118° C. $^1$H NMR (400 MHz, $CDCl_3$) δ 8.05-8.09 (m, 4H), 7.72-7.80 (m, 2H), 7.55-7.64 (m, 4H), 4.57 (t, J=5.2 Hz, 4H), 3.23 (t, J=5.2 Hz, 4H). $^{13}$C NMR (100 MHz, $CDCl_3$) δ 159.2, 138.0, 135.8, 129.8, 128.8, 110.7, 71.5, 47.7. Mass spectrum (API-TIS) m/z 554 ($MH^+$). Anal. calcd for $C_{20}H_{19}N_5O_{10}S_2$: C, 43.39; H, 3.45; N, 12.65. Found: C, 43.26; H, 3.20; N, 12.51.

2b. Ethanamine, 2-[[5-oxido-4-(phenylsulfonyl)-1,2,5-oxadiazol-3-yl]oxy]-N-[2-[[5-oxido-4-(phenylsulfonyl)-1,2,5-oxadiazol-3-yl]oxy]ethyl]-, 2-hydroxy-1,2,3-propanetricarboxylate (1:1) (salt)

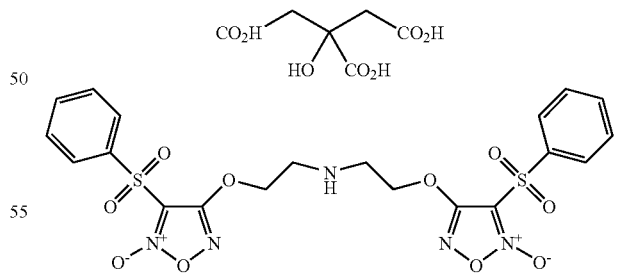

Citric acid (72.9 mg, 0.38 mmol) in MeOH (6 mL) was added to a solution of the product of Example 2a (0.21 g, 0.38 mmol) in a mixture of EtOAc (35 mL) and MeOH (5 mL). The reaction mixture was stirred for at 4° C. for 10 minutes. The residue after evaporation of the solvent was solidified with EtOAc and hexane to give the title compound (0.2 g, 70% yield) as an off-white solid. Mp 60-65° C. $^1$H NMR (400 MHz, DMSO) δ 9.50-10.00 (br S, 2H), 7.95-8.03 (m, 4H), 7.83-7.90 (m, 2H), 7.65-7.75 (m, 4H), 4.51 (br t, J=5.6 Hz, 4H), 3.14 (br t, J=5.6 Hz, 4H), 2.65 (ABq, $J_{AB}$=15.6 Hz, $\Delta\nu_{AB}$=38.8 Hz, 4H). $^{13}$C NMR (100 MHz, DMSO) δ 171.2, 158.9, 137.0, 136.1, 129.9, 128.3, 110.6, 72.1, 70.5, 46.4, 43.0. Mass spectrum (API-TIS) m/z 554 (MH$^+$ for free base), 190 (M-H for citrate). Anal. calcd for $C_{26}H_{27}N_5O_{17}S_2$: C, 41.88; H, 3.64; N, 9.39. Found: C, 41.69; H, 3.41; N, 9.12.

Example 3

Ethanol, 2-[bis[2-[[5-oxido-4-(phenylsulfonyl)-1,2,5-oxadiazol-3-yl]oxy]ethyl]amino]

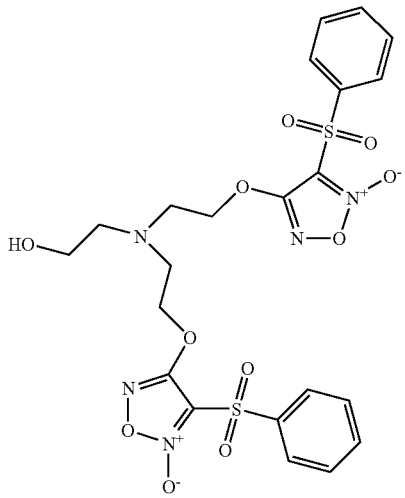

The title compound was prepared as a pale yellow foam (0.5 g, 25% yield) from the product of Example 1b (2.4 g, 6.6 mmol), triethanolamine (Aldrich, 0.43 mL, 0.49 g, 3.28 mmol) and NaOH (50% w/v, 0.5 g, 12.5 mmol) in THF (25 mL) by following the procedure for Example 1c. The crude material was chromatographed on silica gel eluting with (1:1: 0.1) EtOAc:Hex:MeOH. $^1$H NMR (400 MHz, CDCl$_3$) δ 8.02-8.06 (m, 4H), 7.70-7.75 (m, 2H), 7.55-7.62 (m, 4H), 4.55 (t, J=5.2 Hz, 4H), 3.70 (t, J=5.2 Hz, 2H), 3.21 (t, J=5.2 Hz, 4H), 2.91 (t, J=5.2 Hz, 2H), 2.70-2.80 (br s, 1H). $^{13}$C NMR (100 MHz, CDCl$_3$) δ 159.1, 137.8, 135.7, 129.7, 128.7, 128.6, 110.7, 70.0, 59.6, 57.0, 53.0. Mass spectrum (API-TIS) m/z 598 (MH$^+$).

Example 4

1,2,5-Oxadiazole, 3,3',3''-[1,2,3-propanetriyltris(oxy)]tris[4-(phenylsulfonyl)-, 5,5',5''-trioxide

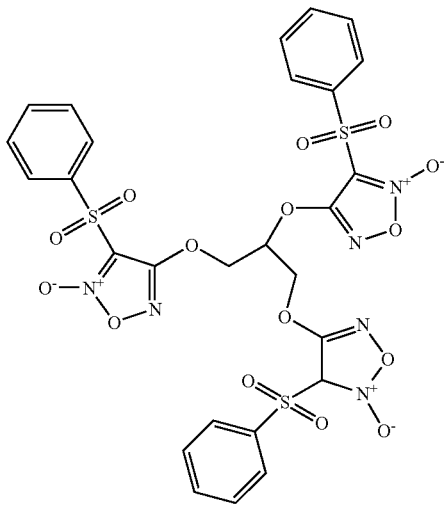

To a mixture of the product of Example 1b (0.79 g, 2.2 mmol) and glycerol (Aldrich, 50 mg, 0.54 mmol) in THF (2 mL) at 0° C. under nitrogen was added dropwise an aqueous solution of NaOH (50% w/v, 0.2 g, 5.0 mmol) and triethylamine (0.2 mL, 0.16 g, 1.6 mmol). The resultant pale-yellow solution was stirred for 3 hours at 0° C. to 4° C. The reaction mixture was then diluted with THF, and the solid was removed by filtration. The residue after evaporation of the solvent was dissolved in warm THF and chromatographed on silica gel eluting with (0.3:0.7 to 1:1) EtOAc:Hex to give the title compound (0.1 g, 18% yield) as a white solid. Mp 68-70° C. $^1$H NMR (400 MHz, CDCl$_3$) δ 8.00-8.10 (m, 6H), 7.70-7.78 (m, 3H), 7.55-7.65 (m, 6H), 5.80-5.85 (m, 1H), 4.90-5.00 (m, 4H). $^{13}$C NMR (100 MHz, CDCl$_3$) δ 158.4, 138.0, 136.0, 135.8, 130.0, 128.9, 128.7, 110.3, 75.4, 67.8. Mass spectrum (API-TIS) m/z 782 (MNH$_4^+$). Anal. calcd for $C_{27}H_{20}N_6O_{15}S_3$: C, 42.41; H, 2.64; N, 10.99. Found: C, 42.69; H, 2.45; N, 10.82.

Example 5

1,2,5-Oxadiazole, 3,3'-[1,2-ethanediylbis(oxy)]bis[4-(phenylsulfonyl)-, 5,5'-dioxide

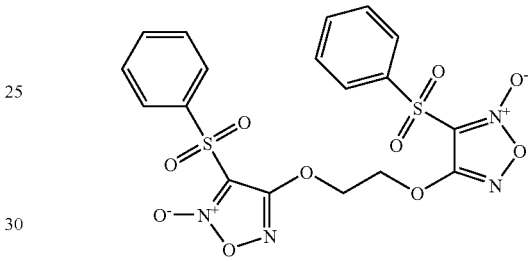

The title compound was prepared as a white solid (0.16 g, 43% yield) from the product of Example 1b (0.53 g, 1.4 mmol), ethylene glycol (Aldrich, 62 µL, 89 mg, 1.4 mmol) and an aqueous solution of NaOH (50% w/v, 0.1 g, 2.5 mmol) in THF (6 mL) by following the procedure for Example 1c. The crude material was dissolved in warm THF and chromatographed on silica gel eluting with (0.3:0.7 to 1:1) EtOAc: Hex to give the title compound (0.16 g, 21% yield) as a white solid. Mp 187-189° C. $^1$H NMR (400 MHz, DMSO) δ 7.95-8.03 (m, 4H), 7.82-7.89 (m, 2H), 7.65-7.72 (m, 4H), 4.81 (s, 4H). $^{13}$C NMR (100 MHz, DMSO) δ 158.7, 137.1, 136.1, 130.0, 128.2, 110.4, 68.7. Mass spectrum (API-TIS) m/z 528 (MNH$_4^+$). Anal. calcd for $C_{18}H_{14}N_4O_{10}S_2$: C, 42.35; H, 2.76; N, 10.97; S, 12.56. Found: C, 42.61; H, 2.50; N, 10.71; S, 12.27.

Example 6

1,2,5-Oxadiazole-3-methanamine, 4-methyl-N-[(4-methyl-5-oxido-1,2,5, oxadiazol-3-yl)methyl]-, 5-oxide

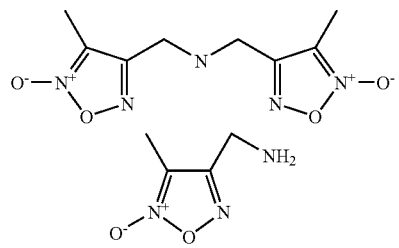

To a solution of 1,2,5-oxadiazole, 4-(bromomethyl)-3-methyl-, 2-oxide (0.8 g, 4.1 mmol, prepared as described in WO 2005/060603 A2, Example 6c) in methanol (1 mL) was added dropwise a solution of NH₃(g) in methanol (5 mL of 2M solution in methanol, 0.16 g, 10 mmol). The reaction mixture was stirred at 0° C. for 3 hours and then at room temperature for 16 hours. The residue after evaporation of the solvent was chromatographed on silica gel eluting with MeOH:EtOAc: CH₂Cl₂ (0.1:1:1) to give the title compound (0.2 g, 20% yield) as a white solid and 1,2,5-oxadiazole-3-methanamine, 4-methyl-, 5-oxide (0.4 g, 75% yield) as an oil.

1,2,5-Oxadiazole-3-methanamine, 4-methyl-N-[(4-methyl-5-oxido-1,2,5, oxadiazol-3-yl)methyl]-, 5-oxide: Mp 60-61° C. $^1$H NMR (300 MHz, CDCl₃) 3.94 (s, 4H), 2.18 (s, 6H). $^{13}$C NMR (75 MHz, CDCl₃) δ 156.0, 112.4, 43.7, 7.8. Mass spectrum (API-TIS) m/z 242 (MH⁺), 483 (M₂H⁺). Anal. calcd for $C_8H_{11}N_5O_4$: C, 39.84; H, 4.59; N, 29.03. Found: C, 39.93; H. 4.34; N, 29.05.

1,2,5-oxadiazole-3-methanamine, 4-methyl-, 5-oxide: $^1$H NMR (400 MHz, d⁶-DMSO) δ 3.80 (s, 2H), 2.29 (br s, 1H), 2.16 (s, 3H). $^{13}$C NMR (100 MHz, d⁶-DMSO) δ 159.9, 112.8, 36.4, 7.1. Mass spectrum (API-TIS) m/z 130 (MH⁺).

Example 7

Vascular Smooth Muscle Cell (SMC) and Endothelial Cell (EC) Antiproliferation Assay Human coronary artery smooth muscle cells (SMC) and endothelial cells (EC) were supplied by Cambrex Bio Science Walkersville, Inc. (Walkersville, MD). The smooth muscle cells were maintained in a basal medium, EBM (Cambrex Bio Science Walkersville, Inc), without phenol red and supplemented with 5% (v/v) fetal bovine serum (FBS), human recombinant epidermal growth factor (EGF), human recombinant fibroblast growth factor (FGF), bovine insulin, 50 µg/mL gentamicin sulfate, and 50 ng/mL amphotericin B (all obtained from Cambrex Bio Science Walkersville, Inc. as SMGM2 SingleQuots). The endothelial cells were grown in a modified EGM2-MV medium (Cambrex Bio Science Walkersville, Inc.), which had the same, phenol red-free, basal medium, EBM, as used in the smooth muscle cell medium, but were supplemented with 5% (v/v) fetal bovine serum (FBS), human recombinant epidermal growth factor (EGF), human recombinant fibroblast growth factor (FGF), vascular endothelial growth factor (VEGF), recombinant insulin-like growth factor-1 (IGF-1), ascorbic acid, 50 µg/mL gentamicin sulfate, and 50 ng/mL amphotericin B (all supplied by Cambrex Bio Science Walkersville, Inc. as EGM2-MV SingleQuots). All cells were incubated under humidified 95% air-5% CO₂ at 37° C. Cells were used for experiments usually up to about 17 cumulative population doublings (i.e., passage 9); and still exhibit their respective traits for smooth muscle or endothelial cells.

For the SMC/EC Antiproliferation Assay, the cells were seeded at 4×10⁴ viable cells in 2 mL of the appropriate medium per well of a Corning tissue culture 24 well plate (Corning, N.Y.). Stock solutions of the test compounds were prepared just prior to addition to the cells by dissolving in DMSO at a concentration 1000 times the highest concentration to be assayed. This stock solution was diluted, as required, with DMSO to the required concentration. On the same day the cells were seeded, but after they had attached and spread out (about 3 hr), each test compound in varying concentrations (2 µL of the diluted stock solutions) was added to four replicate wells (n=4) for each concentration. Control cultures received 2 µL of DMSO per well (n=4). On the following morning, the cultures were examined microscopically and their condition, including evidence of cytotoxicity, recorded. ~68 hours after the addition of the test compound, the cultures were examined microscopically and the viable cells counted with a hemacytometer following trypsinization with 0.25% trypsin-1 mM EDTA. Trypan Blue dye exclusion was used to discriminate between viable and dead cells. The results are presented as % of the control viable cell count (mean±SEM) and are used to determine the IC₅₀ for the inhibition of proliferation of vascular smooth muscle and endothelial cells. IC₅₀ for the test compounds are given in Table 1.

TABLE 1

| Example # | SMC Strain 3033, IC₅₀ | SMC Strain 5286, IC₅₀ | SMC Strain 9557-1, IC₅₀ | EC Strain 3033, IC₅₀ | EC Strain 5675-1, IC₅₀ |
|---|---|---|---|---|---|
| 1d | 6 nM | 17 nM | 8 nM | 447 nM | 460 nM |
| 2b | 71 nM | nd | nd | 690 nM | nd |
| 4 | nd | 13 nM | 9 nM | 346 nM | nd | nd = not determined

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the invention.

What is claimed is:

1. A furoxan compound of Formula (I), or a pharmaceutically acceptable salt thereof:

wherein the compound of Formula (I) is:

(I)

(II)

wherein:
$R_1$ is —$C_6H_4R_2$, —CN, —S(O)₂$C_6H_4R_2$, NO₂ or —C(O)—OR₃;
$R_2$ is hydrogen, —CN, —S(O)₂R₃, NO₂ or —C(O)—OR₃;
$R_3$ is an alkyl group or an aryl group;
T is a covalent bond, oxygen, S(O)ₒ or NR₄;
o is an integer from 1 to 2;
$R_4$ is a hydrogen, a lower alkyl group or an aryl group;
X is —(CH₂)ₐ—N(R₅)(R₆), —(CHR₇)ᵦ—CH₂-T-Z, —(CHR₇)ᵦ—N(R₅)(R₆) or —CH₂—C(CH₂-T-Z)₃;
$R_5$ is a hydrogen, an alkyl group, an aryl group or —(CH₂)ₐ-T-Z;
$R_6$ is a hydrogen, an alkyl group, an aryl group, —(CH₂)ₐ-T-Z or —C(CH₂-T-Z)₃;
$R_7$ is hydrogen or -T-Z;
a is an integer from 2 to 5;
b is an integer from 1 to 6;
Z is

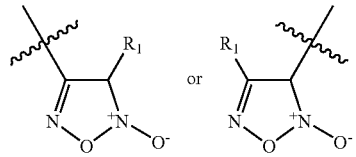

with the proviso that the furoxan compounds of Formula (I) must contain at least one Z group.

2. A composition comprising the compound of claim 1 and a pharmaceutically acceptable carrier.

3. The composition of claim 2, further comprising (i) at least one therapeutic agent; (ii) at least one nitric oxide enhancing compound; or (iii) at least one therapeutic agent and at least one nitric oxide enhancing compound.

4. The composition of claim 3, wherein the therapeutic agent is a thrombolytic agent, an antimicrobial compound, an antiproliferative agent, an antisecretory agent, an anti-cancer chemotherapeutic agent, a steroid, an immunosuppressive agent, a radiotherapeutic agent, a heavy metal functioning as a radiopaque agent, an aldosterone antagonist, an alpha-adrenergic receptor antagonist, an angiotensin II antagonist, an angiotensin-converting enzyme inhibitor, an antidiabetic compound, an anti-hyperlipidemic compound, an antioxidant, an antithrombotic and vasodilator compound, a β-adrenergic antagonist, a calcium channel blocker, an endothelin antagonist, a hydralazine compound, a $H_2$ receptor antagonist, an neutral endopeptidase inhibitor, a nonsteroidal anti-inflammatory compound, a phosphodiesterase inhibitor, a potassium channel blocker, a platelet reducing agent, a proton pump inhibitor, a renin inhibitor, a selective cyclooxygenase-2 (COX-2) inhibitor, or a combination of two or more thereof.

5. The composition of claim 4, wherein the therapeutic agent is at least one compound selected from the group consisting of a thrombolytic agent, an antimicrobial compound, an antiproliferative agent, an anti-cancer chemotherapeutic agent, a steroid, an immunosuppressive agents, an antioxidant, an antithrombotic and vasodilator compound, a hydralazine compound and a platelet reducing agent.

6. A kit comprising at least one compound of claim 1.

7. The kit of claim 6, further comprising further comprising (i) at least one therapeutic agent; (ii) at least one nitric oxide enhancing compound; or (iii) at least one therapeutic agent and at least one nitric oxide enhancing compound.

8. The kit of claim 7, wherein the (i) at least one therapeutic agent; (ii) at least one nitric oxide enhancing compound; or (iii) at least one therapeutic agent and at least one nitric oxide enhancing compound are in the form of separate components in the kit.

9. A compound selected from the group consisting of:
ethanamine, 2-[[5-oxido-4-(phenylsulfonyl)-1,2,5-oxadiazol-3-yl]oxy]-N,N-bis[2-[[5-oxido-4-(phenylsulfonyl)-1,2,5-oxadiazol-3-yl]oxy]ethyl]-;

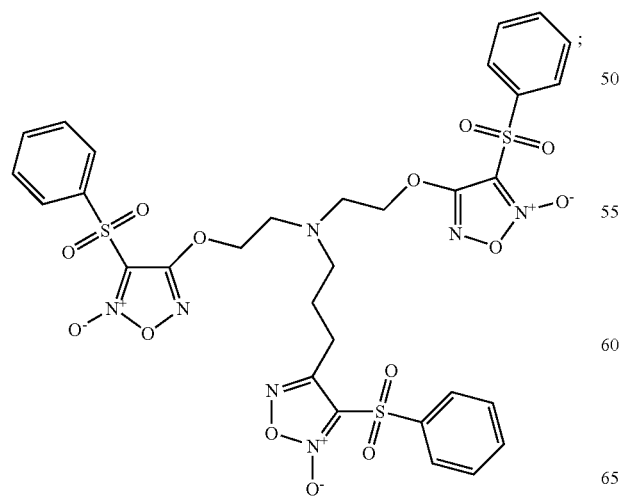

ethanamine, 2-[[5-oxido-4-(phenylsulfonyl)-1,2,5-oxadiazol-3-yl]oxy]-N-[2-[[5-oxido-4-(phenylsulfonyl)-1,2,5-oxadiazol-3-yl]oxy]ethyl]-;

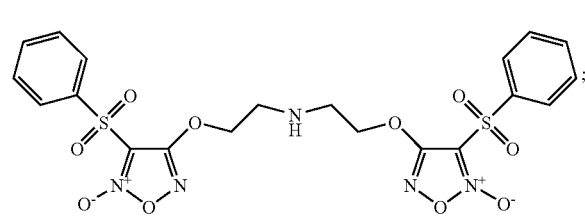

ethanol, 2-[bis[2-[[5-oxido-4-(phenylsulfonyl)-1,2,5-oxadiazol-3-yl]oxy]ethyl]amino]-;

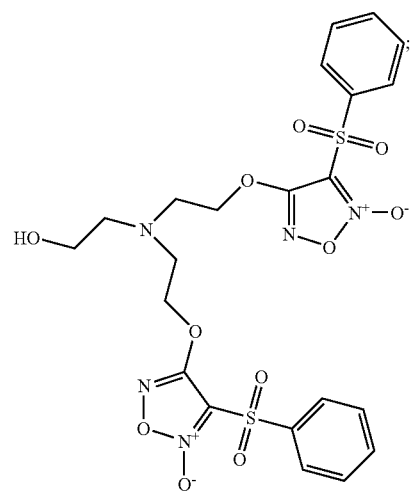

1,2,5-oxadiazole, 3,3',3"-[1,2,3-propanetriyltris(oxy)]tris[4-(phenylsulfonyl)-, 5,5',5"-trioxide;

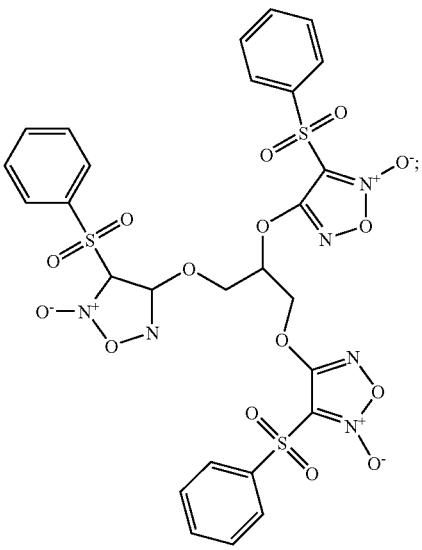

57
1,2,5-oxadiazole, 3,3'-[1,2-ethanediylbis(oxy)]bis[4-(phenylsulfonyl)-, 5,5'-dioxide;
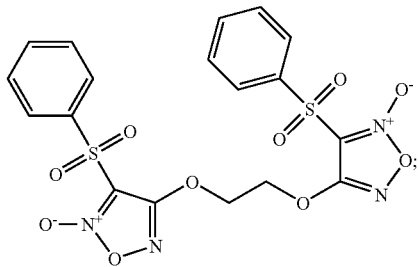
58
1,2,5-oxadiazole-3-methanamine, 4-methyl-N-[(4-methyl-5-oxido-1,2,5, oxadiazol-3-yl)methyl]-, 5-oxide;
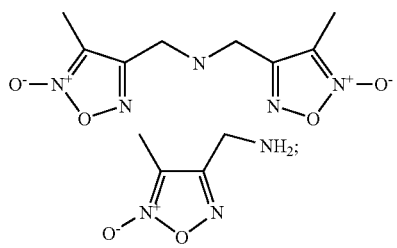
and pharmaceutically acceptable salts thereof.
* * * * *